United States Patent
Zhang et al.

(10) Patent No.: US 11,945,234 B2
(45) Date of Patent: Apr. 2, 2024

(54) LASER-INDUCED CELL TRANSFER AND SORTING

(71) Applicants: Hochschule für angewandte Wissenschaften München, Munich (DE); Universität Regensburg—Universitätsklinikum, Regensburg (DE)

(72) Inventors: Jun Zhang, Munich (DE); Heinz Paul Huber, Oberhaching (DE); Hauke Clausen-Schaumann, Bernried (DE); Stefanie Sudhop, Fahrenzhauen (DE); Denitsa Docheva, Regensburg (DE)

(73) Assignees: Hochschule für angewandte Wissenschaften München, Munich (DE); Universität Regensburg—Universitätsklinikum, Regensburg (DE)

( * ) Notice: Subject to any disclaimer, the term of this patent is extended or adjusted under 35 U.S.C. 154(b) by 316 days.

(21) Appl. No.: 17/413,189

(22) PCT Filed: Dec. 19, 2019

(86) PCT No.: PCT/EP2019/086173
§ 371 (c)(1),
(2) Date: Jun. 11, 2021

(87) PCT Pub. No.: WO2020/127640
PCT Pub. Date: Jun. 25, 2020

(65) Prior Publication Data
US 2021/0339539 A1    Nov. 4, 2021

(30) Foreign Application Priority Data
Dec. 20, 2018    (EP) ..................... 18214358

(51) Int. Cl.
*B41J 2/44* (2006.01)
*C12M 1/26* (2006.01)
*C12Q 1/24* (2006.01)

(52) U.S. Cl.
CPC ............... *B41J 2/44* (2013.01); *C12M 33/00* (2013.01); *C12Q 1/24* (2013.01)

(58) Field of Classification Search
CPC ....... B33Y 80/00; C12M 33/00; C12M 33/04; B01J 2219/00441; B41J 2/442; B41J 2/005; B41M 5/41; A61B 2018/206
See application file for complete search history.

(56) References Cited

U.S. PATENT DOCUMENTS

| 2005/0018036 A1* | 1/2005 | Barron ................. G01N 1/2813 347/224 |
| 2013/0017564 A1* | 1/2013 | Guillemot ............. C12M 33/04 435/8 |

(Continued)

FOREIGN PATENT DOCUMENTS

| ES | 2 360 778 A1 | 6/2011 |
| WO | 2011/107599 A1 | 9/2011 |

OTHER PUBLICATIONS

Barron et al., "Laser Printing of Single Cells: Statistical Analysis, Cell Viability, and Stress," *Annals of Biomedical Engineering* 33(2): 121-130, Feb. 2005.

(Continued)

*Primary Examiner* — John Zimmermann
(74) *Attorney, Agent, or Firm* — Seed IP Law Group LLP

(57) ABSTRACT

A method for transferring objects includes providing a medium in a reservoir, the medium containing objects; providing a substrate having an acceptor surface, the acceptor surface facing an opening of the reservoir; determining a first target focus point in the medium; and generating a first laser pulse or first laser pulse train focused onto the first (Continued)

target focus point. Pulse intensity of the first laser pulse or pulse train at the first target focus point and/or pulse duration of the first laser pulse or pulse train is/are chosen to generate a droplet of the medium ejected towards the acceptor surface. A center wavelength of the first laser pulse or pulse train is larger than 500 nm, larger than 650 nm, or between 0.9 μm and 1.35 μm. The first target focus point is determined relative to the position of at least one object of the objects.

20 Claims, 9 Drawing Sheets

(56) References Cited

U.S. PATENT DOCUMENTS

| | | | |
|---|---|---|---|
| 2015/0224291 A1* | 8/2015 | Guillemot | C12M 21/08 604/290 |
| 2015/0322485 A1* | 11/2015 | Kwon | C12Q 1/6806 506/3 |
| 2020/0009877 A1* | 1/2020 | Viellerobe | C12M 33/00 |
| 2020/0010787 A1* | 1/2020 | Viellerobe | A61F 2/5044 |
| 2022/0009247 A1* | 1/2022 | Arutinov | B41J 2/005 |

OTHER PUBLICATIONS

Duocastella et al., "Novel laser printing technique for miniaturized biosensors preparation," *Elsevier B.V. Sensors and Actuators B* 145: 596-600, 2010.

Hosokawa et al., "Femtosecond Laser Manipulation Techniques for Individual Patterning of Biological Micro-object," *Optical Interactions with Tissue and Cells XIX Edited by Jacques, Steven L.; Roach, William P.; Thomas, Robert J. Proceedings of the SPIE 6854* (article ID 68541K): 1-6, 2008.

Hosokawa et al., "Nondestructive micro-patterning of proteinous occlusion bodies in water by femtosecond laser-induced mechanical force," *Biomed Microdevices* 9: 105-111, 2007.

Koo et al., "Laser-assisted biofabrication in tissue engineering and regenerative medicine," *JMR Early Career Scholars In Materials Science Annual Issue: Review* 32(1), Jan. 2017.

Ringeisen et al., "Jet-based methods to print living cells," *Biotechnology Journal* 1(9): 930-948, Sep. 2006.

Schiele et al., "Laser-based direct-write techniques for cell printing," *Biofabrication* 2(3): 1-15, Jul. 12, 2010.

Serra et al., "Laser-Induced Forward Transfer: Fundamentals and Applications," *Advanced Materials Technologies* 4(1): 1-33, Jan. 2019.

Takahiro et al., "Nondestructive micropatterning of living animal cells using focused femtosecond laser-induced impulsive force," *Applied Physics Letters* 91(2): 023904 1-3, Jul. 13, 2007.

Zhang et al., "Laser induced forward transfer of living cells using femtosecond laser pulses," in *2017 Conference on Lasers and Electro-Optics Europe & European Quantum Electronics Conference* (CLEO/Europe-EQEC), Munich, Germany, Jun. 25-29, 2017, pp. 1-1.

Zhang et al., "Sacrificial-layer free transfer of mammalian cells using near infrared femtosecond laser pulses," PLOS ONE 13(5): 1-11, e0195479. https://doi.org/10.1371/journal.pone.0195479, May 2, 2018.

Colina et al., "DNA deposition through laser induced forward transfer," *Biosensors and Bioelectronics* 20:1638-1642, 2005.

Colina et al., "Laser-induced forward transfer of liquids: Study of the droplet ejection process," *Journal of Applied Physics* 99:7 pages, 2006.

Duocastella et al., "Film-free laser forward printing of transparent and weakly absorbing liquids," *Optics Express* 18(21): 11 pages, 2010.

Duocastella et al., "Laser-induced Forward Transfer of Liquids for Miniaturized Biosensors Preparation," *JLMN—Journal of Laser Micro/Nanoengineering* 3(1):4 pages, 2008.

Duocastella et al., "Novel laser printing technique for miniaturized biosensors preparation," *Sensors and Actuators B* 145:596-600, 2010.

Patrascioiu et al., "Laser-generated liquid microjets: correlation between bubble dynamics and liquid ejection," *Microfluid Nanofluid* 16:55-63, 2014.

Petit et al., "Femtosecond versus picosecond laser pulses for film-free laser bioprinting," *Applied Optics* 56(31):8648-8655, 2017.

Serra et al., "Laser-induced forward Transfer: a Direct-writing Technique for Biosensors Preparation," *JLMN—Journal of Laser Micro/Nanoengineering* 1(3):236-242, 2006.

Serra et al., "Preparation of functional DNA microarrays through laser-induced forward transfer," *Applied Physics Letters* 85(9):1639-1641, 2004.

Vogel et al., "Femtosecond-Laser-Induced Nanocavitation in Water: Implications for Optical Breakdown Threshold and Cell Surgery," *Physical Review Letters* 100:4 pages, 2008.

Zhang et al., "Extending Single Cell Bioprinting from Femtosecond to Picosecond Laser Pulse Durations," *Micromachine*, 12:11 pages, 2021.

Zhang et al., "Method for laser-induced sacrificial layer-free single cell transfer and sorting," *Hochschule München*, 14 pages, 2018.

Zhang et al., "Single Cell Bioprinting with Ultrashort Laser Pulses," *Advanced Functional Materials* 31(19): 10 pages, 2021.

\* cited by examiner

LASER-INDUCED CELL TRANSFER AND SORTING

BACKGROUND

Technical Field

The present invention is in the field of biological and medical technology. In particular, the invention relates to a method and a device to transfer objects, in particular biological objects, onto a substrate.

Description of the Related Art

The precise positioning of biomaterials and in particular biological cells at predetermined locations, e.g., for further investigation, is of great importance for biological and medical applications, for example tissue engineering, biochemical research or medical analysis and diagnosis. Therefore, a variety of bioprinting techniques have been developed, which allow e.g., for the controlled printing of patterns with biological materials, the sorting of cells and even the transfer of single cells from one site or location to another.

This can for example be achieved using microfluidic techniques like block-cell printing or ink-jet printing, see K. Zhang et al., *Proc. Natl. Acad. Sci.* 111, 2948 (2014) and T. Boland et al., *Materials Science and Engineering: C* 27, 372 (2007). Block-cell printing relies on a network of microfluidic channels and microarrays in order to trap single cells at predefined positions, whereas ink-jet printing creates patterns of a medium containing e.g., cells by depositing individual droplets of the medium. These techniques, however, have drawbacks as they can require complex fabrication procedures, e.g., to create the microfluidic network, can strongly depend on properties of the objects to be printed and can be susceptible to clogging of channels or nozzles, which may affect the precision and reliability of the printing.

To overcome these limitations, laser-based techniques have been proposed and implemented in recent years. One example is laser-induced forward transfer (LIFT), which uses tightly focused laser pulses to evaporate an inorganic absorbing layer, on which a medium containing the objects, e.g., biological objects like cells, is deposited, see e.g., A. Piqué et al., *Appl. Phys. A* 69, 279 (1999) and L. Koch et al., *BioNanoMaterials* 15, 71 (2014). The pressure created by the evaporation of the absorbing layer can generate a droplet or jet that is ejected from the medium and may transport objects from the medium onto a substrate. While transferred cells can exhibit a high survival rate, the evaporation of the absorbing layer can lead to contamination of the printed patterns by small fragments of the absorbing layer. Furthermore, the small thickness of the medium containing the objects, which is required to efficiently generate droplets, makes the medium itself prone to uncontrolled evaporation.

Other laser-assisted transfer methods use protein hydrogels as absorbing layers to avoid contamination by inorganic material, see e.g., R. Xiong et al., *Biofabrication* 9, 24103 (2017). Due to the effective absorption of ultraviolet light by proteins, this facilitates the transfer of objects using ultraviolet laser light, but is typically limited to wavelengths below 200 nm, which may cause damage to biological materials, in particular DNA.

A method for stochastically transferring multiple cells from a medium onto a substrate without use of an absorption layer is known from J. Zhang et al., *PLoS ONE* 13(5) (2018). A near-infrared femtosecond laser pulse is focused underneath a cell layer suspended on top of a hydrogel reservoir to generate a jet of material ejected towards the substrate.

A gravity-induced transfer of biological objects between two substrates in water is described in T. Kaji et al., *Appl. Phys. Lett.* 91, 023904 (2007), Y. Hosokawa et al., *Biomed. Microdevices* 9:105 (2017) and Y. Hosokawa et al., *Proc. of SPIE* 6854, 68541K-4 (2008). Femtosecond laser pulses are used to separate objects from a source substrate, to which the objects are initially attached.

BRIEF SUMMARY

The object of the invention is thus to provide a method and a device for transferring objects, in particular biological objects, onto a substrate without contaminating the substrate by inorganic materials and without causing radiation damage to the objects.

This object is met by a method and a device according to claims 1 and 21, respectively. Embodiments of the present invention are detailed in the dependent claims.

The method for transferring objects, preferably biological objects, in particular biological cells, onto a substrate comprises the following steps: (1) providing a medium in a reservoir, wherein the medium contains objects; (2) providing the substrate having an acceptor surface, wherein the acceptor surface faces an opening of the reservoir; (3) determining a first target focus point in the medium; and (4) generating a first laser pulse or first laser pulse train focused onto the first target focus point. The method is characterized in that (a) a pulse intensity of the first laser pulse or first laser pulse train at the first target focus point and/or a pulse duration of the first laser pulse or first laser pulse train is/are chosen such that the first laser pulse or first laser pulse train generates a droplet of the medium that is ejected from the medium towards the acceptor surface; (b) a center wavelength of the first laser pulse or first laser pulse train is larger than 500 nm, preferably larger than 650 nm, most preferably between 0.9 μm and 1.35 μm; (c) a position of at least one of the objects in the medium is determined at least in part; and (d) the first target focus point is determined relative to the position of the at least one object. The numbering of the steps above is for clarity only and does not indicate a certain order of execution. As far as technically feasible, the steps can be permuted and the method and any embodiment thereof can be performed in an arbitrary order of these steps.

This method provides an efficient and gentle way to place objects, e.g., biological objects like cells, from a medium onto a substrate and e.g., allows for a controlled transfer of single cells. In contrast to techniques known from the prior art, the method does not rely on the use of an absorbing material other than the medium containing the objects itself, thereby reducing the risk of contamination. Instead, the pulse intensity and/or the pulse duration of the first laser pulse or first laser pulse train are chosen sufficiently large such that the direct interaction between the first laser pulse or first laser pulse train and the medium gives rise to the creation of the droplet, which can transport objects to the acceptor surface. Furthermore, due to the lack of an absorbing material, the method does not require using a wavelength that is adapted to the absorbing material. This allows for adjusting the center wavelength of the first laser pulse or first laser pulse train in order to minimize the probability of damaging the transferred objects. By using a wavelength in the near-infrared spectrum, in particular between 0.9 μm and 1.35 μm, the absorption rate of the laser light by biological objects can be reduced as compared to ultraviolet light.

Moreover, by determining the position of at least one object and selecting the first target focus point based on this position, the transfer efficiency can be improved and precise control over the number of transferred objects may be achieved.

At first, the substrate and the medium containing the objects are provided. The medium can for example be a liquid or a gel, in particular a hydrogel comprising a mixture of an aqueous solution and an insoluble polymer. The medium may be chosen such that it can sustain biological objects, e.g., cells, for an extended period of time. The medium may exhibit specific optical absorption properties, for example it may be transparent in the visible and/or near-infrared spectrum in order to avoid resonant absorption of the first laser pulse or first laser pulse train. The objects may be added to the medium before or after inserting the medium into the reservoir. A size of the objects may e.g., be between 0.1 µm and 200 µm in every direction. The objects may be biological objects like bacteria, antibodies, proteins, DNA, or other biological molecules. In particular, the biological objects may be biological cells. In other examples, the objects may be inorganic objects, e.g., glass particles. In one example, the objects may be a combination of any of the aforementioned objects.

Typically, the reservoir is oriented such that a surface of the medium facing the opening of the reservoir, which is referred to as "the surface of the medium" in the following, is perpendicular to the direction of gravity. Correspondingly, a plane or direction that is parallel to the surface of the medium is referred to as a horizontal plane or direction, respectively, in the following, whereas the direction perpendicular to the surface of the medium is referred to as the vertical direction. Depending on the viscosity of the medium, however, the orientation of the reservoir may also be chosen such that the surface of the medium facing the opening of the reservoir may not necessarily be perpendicular to the direction of gravity, i.e., the vertical direction as defined above may not be aligned with the direction of gravity or the reservoir is sitting in a no-gravity environment such as space. The reservoir may also be a lab-on-a-chip system. Furthermore, the surface of the medium may not be flat, in which case the vertical direction is defined by the vector corresponding to the average of all normal vectors of the surface of the medium and a horizontal plane is a plane perpendicular to the vertical direction. Note that whenever the terms "horizontal" or "vertical" are used with respect to elements other than the medium, e.g., a motional degree of freedom of the reservoir or the substrate, the skilled person will naturally understand that the corresponding direction or plane is in general fixed relative to the respective element and thus is horizontal or vertical only for an appropriate orientation of the element.

The substrate has an acceptor surface that one or more objects are to be transferred to and can e.g., be a glass slide or a petri dish or a lab-on-a-chip system. Preferably, the substrate is made from a transparent material, but may e.g., also be opaque in other examples. The substrate is placed or mounted such that the acceptor surface faces an opening of the reservoir. Preferably, the acceptor surface is parallel to the surface of the medium exposed by the opening and placed adjacent to this surface, e.g., at a distance of less than 3 mm. The acceptor surface may be flat or may exhibit features like a protrusion or a depression, e.g., a dent, a bump or a groove, or patterns thereof. The acceptor surface may in particular be shaped to facilitate adhesion of objects to the acceptor surface.

Subsequently, the first target focus point is determined, wherein the first target focus point is located in the medium contained in the reservoir. The determination of the first target focus point comprises determining a position of at least one of the objects in the medium at least in part. In the context of this application, determining a position "at least in part" refers to a determination of at least two spatial coordinates of the position. Said position of the at least one object may e.g., be determined along two or three orthogonal directions. For example, the position of the at least one object may be determined along the directions parallel to the acceptor surface and/or the surface of the medium, but may not be determined along the orthogonal direction, e.g., the vertical direction. In particular, a distribution of the objects in the medium may be determined at least in part, wherein said distribution comprises the positions of a plurality of objects. The position of the at least one object may for example be obtained by imaging the at least one object in the medium and extracting the position from said image. In another example, the position of the at least one object in the reservoir may be known beforehand, e.g., by providing the medium in a reservoir comprising microtraps, each of which containing one object, and the position of the at least one object is obtained by determining the position of the reservoir. The position of the at least one object may e.g., be determined manually and/or with automated fitting and/or pattern recognition techniques.

The first target focus point is chosen relative to the position of the at least one object. For example, if the position of one object is determined, the first target focus point may be aligned with the position of the object along one direction, wherein aligning two points along a direction means that a vector connecting the two points is parallel to this direction. The first target focus point can e.g., be aligned with the position of the object along a direction of propagation of the first laser pulse or first laser pulse train or a direction orthogonal to the acceptor surface and/or the surface of the medium. Alternatively, the first target focus point may be aligned with the position of the object along one direction up to an offset, which may be predefined or determined based on the position of other objects. Additionally, the first target focus point may be chosen such that the first target focus point lies at a predefined distance from the object or a surface of the medium. The first target focus point may be constrained to lie within a predetermined plane and only the coordinates within the plane may be chosen relative to the position of the at least one object. If the position of a plurality of objects is determined at least in part, an object to be transferred may be selected from the plurality of objects and the first target focus point may be aligned with the position of the selected object. In another example, the first target focus point may be placed to fulfill a predefined condition, e.g., the presence of a certain number of objects in a predefined area or a minimum distance to neighboring objects. Additionally, a target position on the acceptor surface that one or more objects are to be transferred to may be specified and may be taken into account when determining the first target focus point, for example by aligning the first target focus point with a position of an object in the vicinity of the target position or by choosing the first target focus point such that the object, the target position and the first target focus point lie on a straight line.

The first laser pulse or first laser pulse train is then generated and focused onto the first target focus point. The first laser pulse can be a single continuous laser pulse, e.g., a femtosecond laser pulse. The first laser pulse train may consist of a sequence of laser pulses in close succession, e.g., ten individual femtosecond laser pulses within 1 µs. For simplicity, only the term "first laser pulse" is used in the following, but it should be interpreted as referring to either the first laser pulse or the first laser pulse train. In other words, whenever reference is made to a "laser pulse" herein, this may relate to a single laser pulse or a pattern of closely spaced subsequent pulses without further mention. The first laser pulse has a center wavelength of more than 500 nm, preferably more than 650 nm, most preferably between 0.9 µm and 1.35 µm, in order to reduce the absorption by the objects, in particular for biological objects and other biological material. Here, the center wavelength of the first laser pulse is defined as the wavelength with the maximum light intensity. Depending on the pulse duration, the first laser pulse may have a spectral width exceeding 1 nm, wherein the spectral width is defined as the full width at half maximum of the intensity spectrum of the first laser pulse.

The first laser pulse has a focus at the first target focus point, i.e., the intensity of the first laser pulse exhibits a local maximum in space at the first target focus point. The first target focus point may correspond to a local minimum in a waist, in particular an average waist of the first laser pulse. As the first laser pulse propagates through the medium, the intensity of the first laser pulse increases up to the first target focus point and subsequently decreases again after passing through the first target focus point. The maximum intensity of the first laser pulse at the first target focus point, i.e., the highest intensity that occurs at the first target focus point as the first laser pulse passes through, is referred to as the peak intensity of the first laser pulse in the following. Said intensity is chosen to be so high that an interaction between the light of the first laser pulse and the medium creates a disturbance of the medium. Additionally, the duration of the first laser pulse is sufficiently long such that the disturbance gives rise to a droplet of the medium that is ejected from the medium towards the acceptor surface.

The droplet may e.g., be a single droplet, i.e., a continuous volume filled with the medium that becomes separated from the medium contained in the reservoir, may comprise multiple droplets or may be a jet of the medium traveling from the medium in the reservoir towards the acceptor surface while still being connected to the medium in the reservoir. The droplet can contain one or more objects and can remove them from the medium in the reservoir. Preferably, the droplet is ejected from the medium with a velocity that is sufficient to reach the acceptor surface. When the droplet reaches the acceptor surface, one or more objects contained in the droplet may stick to the acceptor surface.

To generate the droplet, the pulse intensity at the first target focus point may exceed a non-linear photoionization threshold of medium. In this case, the absorption of multiple photons from the first laser pulse may ionize a molecule or an atom from the medium, which may result in an optical breakdown of the medium. Such processes can lead to the formation of a plasma in the vicinity of the first target focus point, which can generate a rapidly expanding cavitation bubble. The expansion of the cavitation bubble may subsequently create the droplet, when the cavitation bubble expands close to the surface of the medium. In one example, the peak intensity of the first laser pulse is approximately $10^{15}$ W/cm$^2$. If the ionization is induced by multi-photon processes, the ionization rate scales non-linearly with the intensity such that the ionization occurs predominantly in the close vicinity of the first target focus point, whereas the remainder of the medium is not perturbed by the first laser pulse. Additionally or alternatively, other processes may contribute to the formation of that droplet, for example a rapid heating of the medium by absorption and emission processes or an expanding pressure wave.

The objects can be located in a surface layer that is in the vicinity of the surface of the medium. This allows for positioning the first target focus point close to the surface and thus can facilitate the generation of the droplet as well as the transfer of the objects by droplet. In one example, the surface layer extends from the surface of the medium to a depth of 50 µm. The surface layer may contain all of the objects in the medium or the majority of the objects in the medium, e.g., more than 80%. To localize the objects in the surface layer, the medium may be a density gradient medium, which has a larger density than the objects and hence generates a buoyancy. In one example, the medium may have a density larger than 1.07 g/ml. The method may comprise incubating the medium in the reservoir, e.g., to ensure that the objects rise to the surface of the density gradient medium.

Preferably, the first target focus point is located on the opposite side of the surface layer as the acceptor surface, i.e., the first target focus point lies in a plane behind, i.e., typically underneath, the surface layer as seen from the acceptor surface. Thereby, the probability that the droplet contains one or more objects can be increased. The first target focus point may be located less than 300 µm, preferably between 50 µm and 100 µm, below the surface of the medium.

In a preferred embodiment, the method comprises imaging the objects in the medium, e.g., to determine the position of the at least one object at least in part. The imaging of the objects may for example be performed with a conventional optical microscope, e.g., by imaging an image plane in the medium with an objective onto an image sensor of a camera, or a confocal microscope. The objects may be labeled with fluorescent markers and may be illuminated for the imaging. The objects may be imaged by single-photon contrast methods, e.g., by measuring the transmission, reflection or scattering of light, by fluorescence imaging or by phase-contrast imaging. Additionally or alternatively, a super-resolution technique such as photoactivated localization microscopy (PALM) or stochastic optical reconstruction microscopy (STORM) may be used. In other examples, a multi-photon imaging technique may be employed, e.g., two-photon fluorescence, coherent anti-Stokes Raman spectroscopy (CARS), second or third harmonic generation or another non-linear contrast generation method. From an image, the distribution of the objects in the medium may be determined at least part, wherein said distribution may e.g., be extracted manually and/or using fitting routines and/or pattern recognition techniques. Imaging the objects may comprise taking multiple images at different points in time, e.g., to confirm that the distribution of objects is stationary. In particular, an image may be taken before and after generating the first laser pulse, for example to confirm that an object has been removed from the medium successfully.

The method may further comprise identifying a single object from the distribution of objects, wherein the single object is spatially isolated from the other objects, e.g., if only one object is to be transferred to the acceptor surface. A object may for example be considered as spatially isolated if there are no other objects within a radius of 50 µm around the object. In another example, the radius may be determined relative to a distance between the surface of the medium and the first target focus point, e.g., if the first target focus point is set to a fixed distance from the surface, the radius may be required to be larger than the fixed distance. The position of the single object can be determined at least in part and the first target focus point can be chosen relative to the position of the single object. For example, the first focus point may be aligned with the position of the single object along one direction, e.g., the vertical direction perpendicular to the surface of the medium, in order to selectively transfer the single object to the acceptor surface with the first laser pulse.

In order to focus the first laser pulse onto the first target focus point, the method can comprise aligning a focus of the first laser pulse to the first target focus point. The focus of the first laser pulse may for example be created by an objective through which the first laser pulse is transmitted. Aligning the focus may comprise changing a distance between the objective and the reservoir, i.e., moving the objective and the reservoir relative to one another. In one example, the reservoir can be displaced along two orthogonal directions, e.g., in the horizontal plane, and the objective may be moved along a third direction, e.g., the vertical direction. In another example, only the reservoir can be moved, whereas the objective is stationary.

Alternatively or additionally, aligning the focus of the first laser pulse may comprise changing a propagation direction of the first laser pulse, in particular a propagation direction before passing through the objective. For example, the incident angle of the first laser pulse on the objective, i.e., the angle between the direction of propagation of the first laser beam in front of the objective and the optical axis of the objective, may be adjusted to change a position of the focus. In another example, a parallel displacement of the first laser pulse in front of the objective may be changed, e.g., to change the direction of propagation of the first laser pulse in the medium while maintaining the position of the focus.

Aligning the focus of the first laser pulse can also comprise changing a spatial intensity pattern and/or a spatial phase pattern of the first laser pulse, e.g., an intensity distribution of the first laser pulse in a plane that is imaged by the objective into the first medium or a phase distribution of the first laser pulse in a plane in front of the objective. In one example, aligning the focus of the first laser pulse involves changing a focal length of a lens, e.g., of an electrically or mechanically adjustable focus-tunable lens.

In a preferred embodiment, the method additionally comprises determining a target position on the acceptor surface and aligning the target position with the first target focus point along one direction. The target position can specify a position on the acceptor surface that an object is to be transferred to. The target position may be obtained as an external input, e.g., as a set of coordinates on the acceptor surface. In another example, determining the target position may involve identifying a feature on the acceptor surface, e.g., a position of an object or a geometrical structure, relative to which the target position is chosen. Determining the target position can involve taking an image of the acceptor surface. To align the target position with the first target focus point, the substrate may be moved with respect to the reservoir, e.g., along two orthogonal directions parallel to the acceptor surface. Additionally, the substrate may be moved in a direction that is perpendicular to the acceptor surface, for example to reach a predefined distance between the acceptor surface and the surface of the medium, e.g., to generate 3d patterns of transferred liquids and/or objects.

The acceptor surface of the substrate may be coated with a cushioning film, in particular an extracellular matrix gel. The cushioning film may dampen the impact of landing objects, facilitate adhesion of the objects and/or provide a humidified environment for the objects on the acceptor surface. The thickness of the coating layer may for example be in the range of 50 µm to 150 µm. Additionally, the acceptor surface may be roughened, patterned or structured to facilitate adhesion. In one example, the acceptor surface may be a part of a lab-on-a-chip system.

A diameter of the first laser pulse at the first target focus point can be smaller than 5.0 µm, preferably smaller than 2.0 µm. This may be achieved by using an objective with a large numerical aperture, e.g., a numerical aperture exceeding 0.5, and/or a large diameter of the first laser pulse in front of the objective. The diameter of the first laser pulse at the first focus point may be adapted to the pulse energy and/or the pulse duration of the first laser pulse in order to achieve an intensity at the first target focus point that is sufficient for the generation of the droplet. Choosing a small diameter at the first target focus point may also reduce the intensity at the position of an object outside of the focus due to a stronger divergence of the tightly focused first laser pulse.

In a preferred embodiment, the first laser pulse is a femtosecond laser pulse with a pulse duration between 1 fs and 1 ps, in particular between 300 fs and 700 fs. Alternatively, the first laser pulse, i.e., the first laser pulse train, can be a sequence of femtosecond laser pulses, preferably femtosecond laser pulses with a pulse duration between 300 fs and 700 fs. The pulse duration may be chosen based on the medium. For example, when a medium with a higher non-linear photoionization threshold is used, a shorter pulse duration may be selected than for a medium with a lower non-linear photoionization threshold to increase the intensity of the first laser pulse at the first target focus point. In some examples, the pulse duration may be longer than 1 ps, e.g., up to 10 ns.

The center wavelength and/or a spectral width of the first laser pulse may be adapted to an absorption spectrum of the objects, e.g., to reduce the probability of damaging the objects by the first laser pulse. For example, a local minimum in the absorption spectrum may be determined and the center wavelength may be set to the wavelength at which the minimum in the absorption spectrum occurs. Additionally, the spectral width may be chosen such that the entire wavelength spectrum of the first laser pulse is close to the minimum. In another example, the center wavelength may be within a range in which biological tissue is known to exhibit little absorption and laser sources with a sufficiently large output power are available, e.g., in the near-infrared window between 0.9 µm and 1.35 µm, where an absorption coefficient of biological tissue may be more than an order of magnitude smaller than in the ultraviolet spectrum between 200 and 400 nm. The center wavelength may further be adapted to the medium containing the objects, e.g., to avoid electronic excitation in the UV spectrum, e.g., below 200 nm, and resonant excitation of vibrational transitions in water molecules in the mid-infrared spectrum above 1.35 µm.

In one example, the medium can contain different types of objects, e.g., a first and a second type of cells. In this case, determining the position of the at least one object may comprise determining the type of the at least one object, i.e., to distinguish whether the at least one object is of a first type or a second type. The type of an object may for example be determined from a size and/or a shape of the object. In another example, the objects may be labeled by object-type specific markers, e.g., fluorescent labels with different characteristic wavelengths, which may additionally be used for the determination of the position of the at least one object. To determine the type of the at least one object, any one of the imaging methods described above may be used, e.g., single-photon or multi-photon contrast methods. The determination of the object type may be performed manually or automated with an image recognition algorithm that may comprise an artificial intelligence. This can allow for the transfer of objects of a certain type, for which the type of the at least one object may be taken into account when determining the first target focus point. For example, a single cell of a certain type may be identified from a distribution of the cells and its position may be determined in order to set the first target focus point relative to the position of this single cell.

The reservoir and/or the acceptor surface may be lab-on-a-chip systems, e.g., lab-on-a-chip systems configured to provide a constant flow of cell media. Laser pulses may be used to identify a special type of object in the medium flowing in the reservoir. The first target focus point may be determined such that the first laser pulse transfers one or more objects of that special type to the acceptor surface. A flow of a cell medium may also be generated on the acceptor surface. By that means e.g., cell sorting and separation may be performed.

The method may further comprise generating a second laser pulse and focusing the second laser pulse onto a second target focus point in the medium. The second target focus point can be determined relative to the position of the at least one object similar to the first target focus point. In one example, two objects are identified from the distribution of the objects in the medium, their positions are determined at least in part and the first target focus point is aligned with the position of one of the objects and the second target focus point is aligned with the position of the other object. The first laser pulse and the second laser pulse may be generated simultaneously, e.g., by splitting a single laser pulse. Alternatively, the first laser pulse and the second laser pulse may be separate laser pulses emitted by the same laser source. Different target positions on the acceptor surface may be specified for the first laser pulse and the second laser pulse and may be aligned with the respective target focus point prior to generating the respective laser pulse. The first laser pulse and the second laser pulse can be identical and in particular can have the same pulse duration, pulse energy and/or center wavelength. The second laser pulse may also be a second laser pulse train.

In a similar fashion, the method may be extended to include an arbitrary number of laser pulses, each of which may be focused to a different target focus point. The method may for example also comprise generating a plurality of laser pulses focused onto a plurality of target focus points in the medium to create a structure comprising a plurality of objects on the acceptor surface. The plurality of laser pulses and the plurality of focus points may e.g., comprise more than ten laser pulses and more than ten focus points, respectively, in some examples more than 100 laser pulses and more than 100 focus points, respectively. Each of the target focus points may be determined relative to the position of the at least one object. In one example, the plurality of objects is identified from the distribution of the objects in the medium, the positions of the plurality of objects are determined at least in part and the each target focus point is aligned with the position of one of the plurality of objects. Different target positions on the acceptor surface may be specified for each of the laser pulses and may be aligned with the respective target focus point prior to generating the respective laser pulse. This may e.g., be used for high throughput 3d bioprinting or sorting of cells. The target positions may be in particular be chosen such that a particular structure comprising the plurality of objects is created on the acceptor surface. The structure may for example be a 2d or 3d pattern of objects, e.g., a periodic pattern.

In addition, the method can comprise focusing a laser beam onto a third target focus point in the medium. The laser beam may be a continuous wave laser beam, a pulsed laser beam or a single laser pulse. The laser beam may be generated from the same laser source as the first laser pulse and/or the second laser pulse or may be generated from a different laser source. The laser beam may for example be used as an optical tweezer to trap objects or as a cutting beam, e.g., to isolate cells from a larger piece of tissue. In particular, the third target focus point may be moved while the laser beam is focused on the third target focus point. For example, an initial third target focus point may be chosen, e.g., relative to the position of the at least one object, and subsequently may be moved to the first target focus point or the second target focus point while the laser beam is on. In some examples, the third target focus point may be within the substrate or on or adjacent to the acceptor surface, for example to perform subtractive or additive laser processing of the substrate or a medium on the substrate, e.g., by laser ablation or multi-photon polymerization.

The present invention also provides a device for transferring objects, preferably biological objects, in particular biological cells, onto a substrate, which may be used to implement the method according to the invention or an embodiment thereof. The device comprises (1) a reservoir for holding a medium, in particular a medium containing objects; (2) a substrate holder configured to hold the substrate having an acceptor surface such that the acceptor surface faces an opening of the reservoir; (3) a laser source configured to emit laser pulses; (4) a control unit for generating a first laser pulse from the laser source; and (5) an objective for focusing the first laser pulse onto a focus of the first laser pulse. The device according to the present invention is characterized in that (a) the control unit comprises an imaging module configured to determine a position of at least one of the objects in the medium at least in part; (b) the control unit is configured to determine a first target focus point relative to the position of the at least one object; (c) the control unit comprises a focusing module configured to align the focus of the first laser pulse to the first target focus point; (d) a center wavelength of the first laser pulse is larger than 500 nm, preferably larger than 650 nm, most preferably between 0.9 μm and 1.35 μm; and (e) a pulse intensity at the first target focus point and a pulse duration of the first laser pulse are sufficiently large such that the first laser pulse generates a droplet of the medium that is ejected from the medium towards the acceptor surface.

The reservoir is configured to hold the medium containing the objects and can be made of an impermeable material like glass or plastic. Preferably, the reservoir is transparent in the visible and/or near-infrared spectrum as well as capable of withstanding high light intensities. The reservoir has an opening on one side, e.g., the top, and can for example be formed like a cylindrical dish, a cylindrical laboratory beaker or a rectangular box. The reservoir may be removable from the device as a whole or in parts. The reservoir may be a lab-on-a-chip system. The lab-on-a-chip system may for example be configured to supply a constant flow of fresh cell-laden medium, e.g., for high throughput 3d bioprinting of cells. High throughput 3d bioprinting of cells may e.g., be used to create parts of organs or biological structures from multiple cells.

The substrate holder is configured to hold the substrate that the objects are to be transferred to. To this end, the substrate holder is configured for the substrate to be placed or mounted in the substrate holder such that the acceptor surface of the substrate faces the opening of the reservoir. The substrate holder as a whole or in parts can be removable from device. Furthermore, the substrate holder may be configured to move the substrate and/or rotate the substrate. The substrate may be a lab-on-a-chip system. The lab-on-a-chip system may be configured to supply a constant flow of fresh cell-laden medium, e.g., for high throughput 3d bioprinting of cells, e.g., to create parts of organs or biological structures from multiple cells.

The laser source is configured to emit laser pulses and serves as the source of the first laser pulse. The laser source can be a pulsed laser, in particular a femtosecond laser, or may alternatively be a continuous wave laser whose output is modulated in time to generate pulses. The laser source is configured to emit laser pulses with a pulse energy that is sufficiently large for the first laser pulse to generate the droplet ejected from the medium if focused appropriately. In one example, the laser source may emit laser pulses with a pulse energy of more than 1 µJ, preferably more than 5 µJ. The laser source is configured to emit laser pulses with a center wavelength of more than 500 nm, preferably 650 nm, most preferably between 0.9 µm and 1.35 µm. The laser source may have a tunable wavelength.

The control unit is configured to generate the first laser pulse from the laser source. Here and in the following, "generating" a laser pulse or laser beam "from the laser source" refers to controlling the laser source or the light emitted by the laser source in order to create the laser pulse or laser beam, respectively, from the light emitted by the laser source. For this, the control unit can be coupled to a pulse shaping unit, which may for example be configured to transmit a single laser pulse of a sequence of laser pulses emitted from the laser source, e.g., in response to a trigger signal received from the control unit. The pulse shaping unit may comprise one or more optical switching elements, e.g., an acousto-optic modulator an electro-optic modulator and/or a mechanical shutter. The pulse shaping unit may be part of the laser source.

The first laser pulse passes through the objective, which focuses the first laser pulse onto the focus of the first laser pulse. Preferably, the objective is placed such that a focal point of the objective lies within the reservoir and that the substrate, when mounted in the substrate holder, is between the objective and the focal point of the objective. The effective focal length of the objective and/or the diameter of the first laser pulse in front of the objective are chosen such that the light intensity of the first laser pulse is sufficiently large at the focus to generate the droplet ejected from the medium. The objective can be a single lens or can comprise a plurality of lenses. The objective may be a high-NA objective having a numerical aperture exceeding 0.5 and may have a working distance larger than 3 mm. In some examples, the objective may be an immersion objective, e.g., an oil-immersion objective with a numerical aperture above 1.0. The objective may be corrected at least in part for elements between the objective and the focal point of the objective, e.g., the substrate, the reservoir or the medium.

The control unit is further configured to determine the first target focus point. For this, the control unit comprises the imaging module that is configured to determine the position of the at least one object in the medium at least in part. The imaging module may be configured to analyze one or more images of the objects in the medium, e.g., to determine the position of an object via a fit and/or with a pattern recognition technique. The imaging module may further be configured to receive input from a user, for example a region of interest, in which the positions of the objects are to be determined. The control unit is configured to obtain the position of the at least one object from the imaging module in order to determine the first target focus point as described above. The imaging module may be implemented in software, hardware or a combination thereof.

In order to focus the first laser pulse onto the first target focus point determined by the control unit, the control unit comprises the focusing module, which is configured to control the position the focus of the first laser pulse. To this end, the focusing module may receive the first target focus point from the control unit as well as the current position of the focus of the first laser pulse. The current position of the focus corresponds to the point onto which the first laser pulse would be focused in the current state of the device. The focusing module is configured to move the focus of the first laser pulse such that it is aligned to the first target focus point, i.e., the position of the focus is equal to the first target focus point. The focusing module can for example be configured to adjust the focus of the first laser pulse in the horizontal plane. Additionally, the focusing module may be configured to adjust the focus of the first laser pulse in the vertical direction. To move the focus of the first laser pulse, the focusing unit can be configured to control one or more movable or adjustable elements, e.g., the reservoir and/or the objective. To perform the alignment, the focusing module may be configured to perform an active feedback by continuously monitoring the current position of the focus, e.g., by generating and imaging alignment pulses with a low intensity. The focusing module may be implemented in software, hardware or a combination thereof.

In a preferred embodiment, the device is configured to generate a first laser pulse with a pulse intensity that exceeds a non-linear photoionization threshold of the medium. For example, the device may be capable to generate a first laser pulse with a peak intensity at the first focus point larger than $10^{13}$ W/cm$^2$, preferably larger than $10^{14}$ W/cm$^2$.

To align the focus of the first laser pulse to the first target focus point, the focusing module can be configured to control the position the focus of the first laser pulse by changing a distance between the objective and the reservoir. The reservoir and/or the objective can be mounted on translation stages that are controlled by the focusing module and are configured to move the reservoir and the objective, respectively, along at least one direction. The reservoir may also be mounted on a rotation stage that is controlled by the focusing module and configured to rotate the reservoir around at least one axis. Additionally or alternatively, the focusing module may be configured to change a propagation direction of the first laser pulse. For this, the focusing module may be configured to control one or more adjustable optical elements, for example an adjustable mirror with actuators controlled by the focusing module, e.g., a galvanometer scanner, or an acousto-optic deflector, wherein a frequency of a radio-frequency drive signal for the acousto-optic deflector is set by the focusing module. The focusing module may also be configured to change a spatial intensity pattern and/or a spatial phase pattern of the first laser pulse, e.g., via a spatial light modulator like a digital micromirror device or a liquid crystal array. Furthermore, the focusing module can be configured to change a focal length of a lens, e.g., an electrically or mechanically controlled focus-tunable lens.

In one example, the device can further comprise an imaging system and a camera for imaging the objects in the medium. The imaging system can be configured to image a plane in the reservoir onto a sensor chip of the camera, for example by forming a conventional optical microscope or a confocal microscope in conjunction with the objective. The camera may for example be a CCD camera, a CMOS camera or a photodiode. Additionally, the device may comprise a light source for illuminating the objects in the medium. The light source may in particular be a laser source or narrow-band light source configured to drive single-photon effects, e.g., to excite fluorescent labels attached to the objects, or multi-photon effects. The imaging system may further be configured to image the acceptor surface of the substrate. The light source, imaging system and/or camera may be configured to image the objects by single-photon contrast methods, e.g., by measuring the transmission, reflection or scattering of light, by fluorescence imaging or by phase-contrast imaging. In other examples, the light source, imaging system and/or camera may be configured to image the objects by a multi-photon imaging technique, e.g., two-photon fluorescence, coherent anti-Stokes Raman spectroscopy (CARS), second or third harmonic generation or another non-linear contrast generation method.

In a preferred embodiment, the imaging module is configured to determine a distribution of the objects at least in part, i.e., to determine the positions of a plurality of objects at least in part. For this, the imaging module may be configured to receive an image of the objects in the medium from the camera and extract the positions of the objects from the image. The imaging module can further be configured to identify a single object from the distribution of the objects as described above and to determine its position at least in part, wherein the single object is spatially isolated from the other objects. To this end, the imaging module may be configured to calculate inter-object distances from the distribution of the objects and to find the object with the largest distance to the closest object in its vicinity. The imaging module may also be configured to receive specifications, e.g., from a user, for the identification of the single object, for example a region of interest that the single object should be located in or a threshold radius specifying a minimum distance to the closest object in the vicinity.

The control unit can also be configured to move the substrate, in particular to align a target position on the acceptor surface with the first target focus point. The control unit may for example receive the target position via an external input or from the imaging module, which may be configured to identify the target position from an image of the acceptor surface as described above. The substrate holder may comprise a translation stage for moving the substrate along at least one direction and/or a rotation stage for rotating the substrate around at least one axis.

In one example, the device is configured to focus the first laser pulse at the first focus point to a diameter that is smaller than 5.0 µm, preferably smaller than 2.0 µm. Furthermore, the laser source can be configured to emit femtosecond laser pulses, preferably with a duration between 300 femtoseconds and 700 femtoseconds. The laser source may be configured to emit single pulses or to periodically emit the laser pulses with a fixed repetition rate, for example with a repetition rate of 100 kHz.

In a preferred embodiment, the control unit is configured to adjust the center wavelength, a spectral width, the pulse duration and/or a pulse energy of the first laser pulse. To control the pulse energy of the first laser pulse, the control unit may be coupled to the laser source to adjust the pulse energy of the laser pulses emitted by the laser source or the pulse shaping unit may be configured to adjust an attenuation for the first laser pulse. To change the pulse duration, the pulse shaping unit may for example comprise a dispersive element, e.g., a prism-based or grating-based pulse stretcher.

The imaging module may further be configured to determine a type of at least one of the objects in the medium, e.g., by analyzing a color, a size and/or a shape of the objects on images received from the camera, by taking multiple images of the objects with excitation light of different wavelengths generated from the light source or by exploiting multi-photon effects.

In one example, the control unit is configured to determine a second target focus point relative to the position of the at least one object as described above and to generate a second laser pulse from the laser source. The second laser pulse may be spatially and/or temporally separated from the first laser pulse. The pulse shaping unit may for example be configured to transmit the first laser pulse when receiving a first trigger signal from the control unit and to transmit the second laser pulse when receiving a second trigger signal from the control unit. Alternatively, the control unit may be configured to spatially split a single laser pulse emitted by the laser source, e.g., using a beam splitter, an acousto-optic modulator or a spatial light modulator. The control unit can be configured to independently control parameters of the first laser pulse and the second laser pulse, e.g., the pulse energy and/or the pulse duration. Furthermore, the focusing module can be configured to align the focus of the second laser pulse to the second target focus point similar to the alignment to the first target focus point.

The control unit can also be configured to generate a laser beam from the laser source and to determine a third target focus point, wherein the focusing module may be configured to align the focus of the laser beam to the third target focus point. The third focus point may e.g., be located in the reservoir, on or adjacent to the acceptor surface or in the substrate. Preferably, the focusing module is configured to change the focus of the laser beam while the laser beam is on. In another example, the device may comprise an additional laser source to generate the laser beam. The laser beam may be a continuous wave laser beam, a pulsed laser beam or a single laser pulse. The control unit may be configured to control a pulse duration, a pulse energy and/or a power of the laser beam. The control unit and the focusing unit may in particular be configured to perform subtractive or additive laser processing of the substrate or a medium on the substrate, e.g., by laser ablation or multi-photon polymerization.

The device can further comprise a transfer chamber containing the reservoir and the substrate mounted in the substrate holder. The transfer chamber may in particular be a temperature-controlled incubation chamber, wherein the control unit can be configured to actively regulate the temperature in the incubation chamber. In another example, the device may comprise a temperature-controlled incubation chamber that is separate from the transfer chamber and may be configured to move the substrate from the transfer chamber to the incubation chamber.

BRIEF DESCRIPTION OF THE SEVERAL VIEWS OF THE DRAWINGS

In the following, a detailed description of the invention and exemplary embodiments thereof is given with reference to the figures. The figures show schematic illustrations of FIG. 1: a device for transferring objects onto a substrate according to an exemplary embodiment of the invention;

FIG. 2b-2f: a laser-induced transfer of a single cell according to an embodiment of the invention;

DETAILED DESCRIPTION

Figure 1:
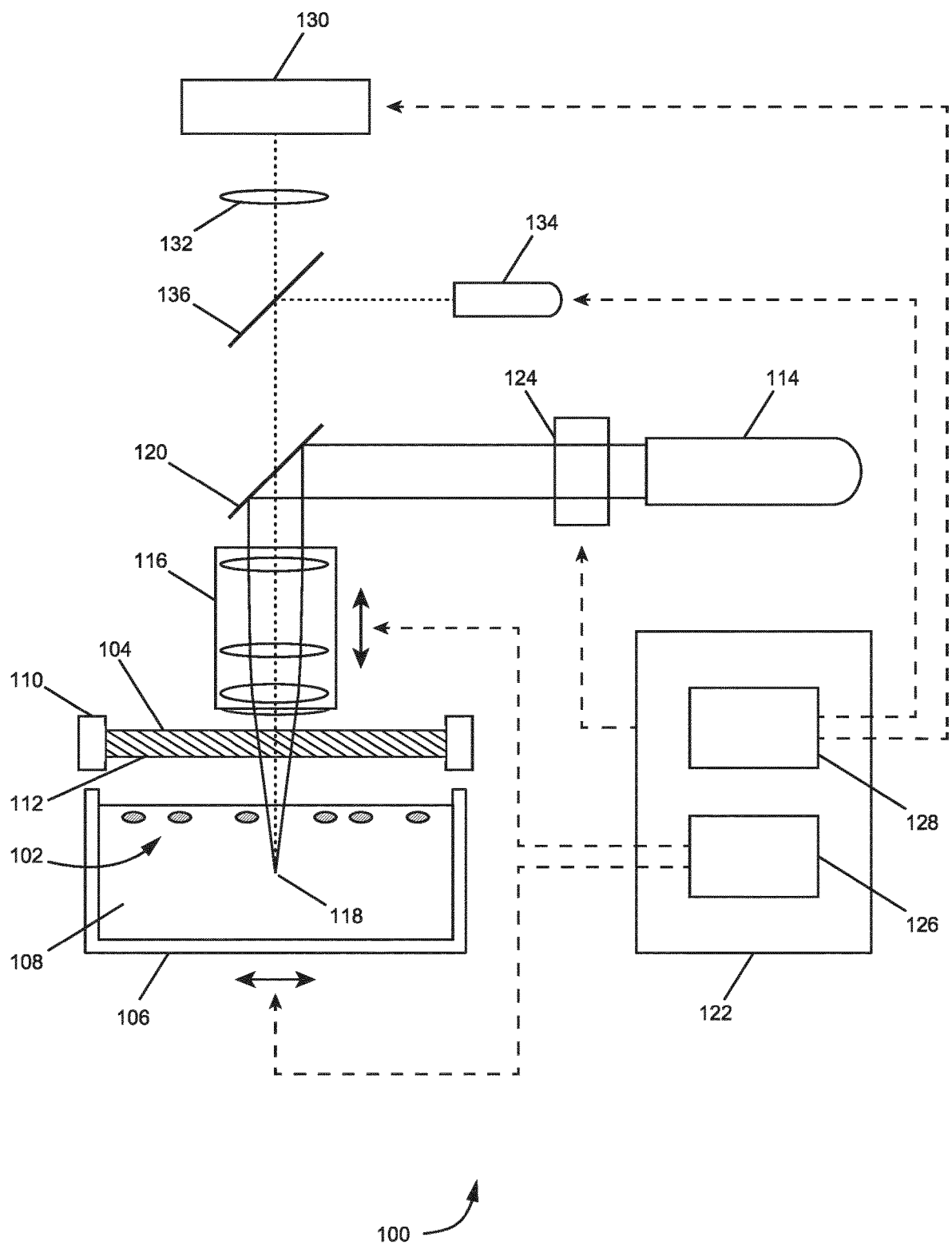

FIG. 1 depicts a device 100 for transferring objects 102 onto a substrate 104 according to an exemplary embodiment of the invention. In the following, a number of examples are described, in which the objects 102 are biological cells. This is, however, not intended to be limiting in any way. In other examples, the objects 102 can be inorganic objects like glass particles or biological objects like cells, bacteria, antibodies, proteins or other biological molecules, or a combination thereof. The device 100 comprises a reservoir 106, which can for example be shaped like a cylindrical dish, a cylindrical laboratory beaker or a rectangular box with an opening on one side. The reservoir 106 can be made of an impermeable material like glass or plastic, which preferably is transparent in the visible and near-infrared spectrum and is capable of withstanding high light intensities. The reservoir 106 is configured to hold a medium 108 that contains the cells 102. The reservoir can be a lab-on-a-chip system, e.g., a lab-on-a-chip system configured to provide a constant flow of medium. The reservoir 106 as a whole or in parts may be removable from the device 100, e.g., to fill the medium 108 into the reservoir 106. The medium 108 can be a liquid or a gel, in particular a hydrogel comprising a mixture of an aqueous solution and an insoluble polymer. The medium 108 may be a gradient medium with a density that is larger than the density of the cells 102 in order for the cells 102 to accumulate in a surface layer in the vicinity of a surface of the medium 108. Preferably, the medium 108 is transparent in the visible and near-infrared spectrum.

Typically, the reservoir 106 is oriented such that the medium 108 is contained in the reservoir 106 and that the surface of the medium 108, i.e., the surface of the medium 108 facing the opening of the reservoir 106, is perpendicular to the direction of gravity. As defined above, a plane or direction that is parallel to the surface of the medium 108 is thus referred to as a horizontal plane or direction, respectively, in the following, whereas the direction perpendicular to the surface of the medium 108 is referred to as the vertical direction. Depending on the viscosity of the medium 108, however, the orientation of the reservoir 106 may also be chosen such that the surface of the medium 108 facing the opening of the reservoir 106 may not necessarily be perpendicular to the direction of gravity, i.e., the vertical direction as defined above may not be aligned with the direction of gravity.

The device 100 further comprises a substrate holder 110, in which the substrate 104 can be mounted such that an acceptor surface 112 of the substrate 104 faces the opening of the reservoir 106. The substrate holder 110 as a whole or in parts may be removable from the device 100, e.g., to place or mount the substrate 104 thereon. The substrate holder 110 may further be configured to move the substrate 104, e.g., in two or three orthogonal directions, and/or rotate the substrate 104. For this, the substrate holder 110 may comprise a translation and/or rotation stage (not shown).

In addition, the device 100 comprises a laser source 114 that is configured to emit laser pulses. The laser source 114 can be a pulsed laser, e.g., a Q-switched laser or a mode-locked laser, in particular a femtosecond laser. Alternatively, the laser source 114 may be a continuous wave laser whose output is modulated in time to generate pulses, e.g., using an acousto-optic and/or electro-optic modulator. The center wavelength of the laser source 114 is larger than 500 nm, preferably larger than 650 nm, and can for example be in the range of 0.9 µm to 1.35 µm. The center wavelength may further be adapted to an absorption spectrum of biological cells, wherein the absorption spectrum can characterize the absorption of light by a specific type of biological cells, e.g., the cells 102, or by a variety of biological cells of different types as a function of the wavelength of the light. Preferably, the center wavelength is chosen such as to minimize absorption of the laser light by the cells 102, e.g., by selecting a wavelength at or close to a minimum in the absorption spectrum. The laser source 114 can for example be a Ti-doped: laser, a Yb-doped laser, or a Nd-doped laser. The center wavelength of the laser source 114 may be tunable, for example by employing a tunable Ti:Sapphire laser or non-linear wavelength generation, e.g., to facilitate an adjustment of the center wavelength to the absorption spectrum.

The laser source 114 is configured to emit laser pulses with a sufficiently large pulse energy and a sufficiently short pulse duration such that a laser pulse, when focused to an appropriate diameter and an appropriate position within the medium 108, generates a droplet of the medium 108 that is ejected from the reservoir 106 as described in more detail below. This can for example occur due to photoionization of the medium 108 or one of the constituents of the medium 108 by the laser pulse, which may lead to an optical breakdown of the medium 108. Preferably, the laser pulse induces non-linear photoionization through multi-photon processes such that the photoionization rate depends non-linearly on the light intensity and thus increases drastically in the vicinity of a focus of the laser pulse. To this end, the center wavelength of the laser source 114 may further be adapted to absorption properties of the medium 108, in particular to avoid resonant single-photo absorption. The pulse energy of the laser pulses can be larger than 1 µJ, preferably larger than 5 µJ, and the pulse duration of the laser pulses can be shorter than 1 ps, preferably in the range between 300 fs and 700 fs. In particular, the pulse energy and the pulse duration may be adapted such that a pulse intensity at a focus of the laser pulse is higher than a non-linear photoionization threshold of the medium.

The device 100 comprises an objective 116 for focusing light emitted by the laser source 114 onto a focus 118. Along the optical path between the laser source 114 and the objective 116 a variety of optical elements may be placed, for example a mirror 120. The mirror 120 may be adjustable in order to align the optical path onto the objective 116. Alternatively or additionally, the device 100 may comprise other adjustable optical elements, e.g., a galvanometer scanner, an acousto-optic deflector or an electro-optic deflector. In addition, refractive elements like lenses may be used to adjust a diameter of the pulses emitted by the laser source 114, e.g., to obtain a collimated beam in front of the objective 116. The effective focal length of the objective 116 and the diameter of the laser pulses in front of the objective 116 are chosen such that the light intensity of a laser pulse with the pulse energy and the pulse duration provided by the laser source 114 is sufficiently large at the focus 118 to generate the droplet of the medium as described above. The objective 116 may for example have a numerical aperture larger than 0.4, e.g., 0.6. In some examples, the objective 116 may be an immersion objective, e.g., an oil-immersion objective with a numerical aperture larger than 1.0. The size of a laser pulse focused by the objective 116 onto the focus 118 may for example be between 1 µm and 2 µm depending on the center wavelength, the focal length of the objective and the diameter of the laser pulse in front of the objective 116. Preferably, the objective 116 is placed above the reservoir 106 such that the optical axis of the objective 116 is perpendicular to the surface of the medium 108, i.e., the optical axis of the objective 116 is parallel to the vertical direction. In other examples, however, the optical axis of the objective 116 may be tilted with respect to the vertical direction, e.g., by an angle of less than 10°. Alternatively, the objective 116 may also be placed underneath the reservoir 106 in an inverted microscope configuration or may be facing a side of the reservoir 106, in particular a vertical side, wherein the optical axis of the objective 116 may be parallel to the horizontal plane. This may e.g., be advantageous to facilitate mounting and removal of the substrate.

Furthermore, the device 100 contains a control unit 122, which is configured to generate a first laser pulse from the laser source 114, i.e., to control the laser source 114 or the light emitted by the laser source 114 in order to create the first laser pulse. The first laser pulse may be a single continuous laser pulse or closely spaced succession of multiple laser pulses, i.e., a first laser pulse train. In order to do this, the control unit 122 can be coupled to a pulse shaping unit 124, which may be configured to generate the first laser pulse from a continuous stream of laser pulses emitted by the laser source 114, e.g., by only transmitting a single laser pulse or a pulse train comprising a plurality of successive pulses. The pulse shaping unit 124 may comprise one or more optical switching elements like an acousto-optic modulator, an electro-optic modulator and/or a mechanical shutter. In one example, the pulse shaping unit 124 may be integrated into the laser source 114, e.g., to modulate a continuous wave laser beam or as an active Q-switch. The pulse shaping unit 124 may be configured to generate the first laser pulse after receiving a trigger signal from the control unit 122. In addition, the pulse shaping unit 124 may be configured to change a temporal profile and/or a pulse duration of a laser pulse emitted by the laser source 114 in order to generate the first laser pulse, e.g., with a dispersive element. The control unit 122 may be configured to control the pulse energy of the first laser pulse, e.g., by controlling an attenuation of the first laser pulse through the pulse shaping unit 124 or by controlling an output power of the laser source 114.

The control unit 122 may be configured to generate additional laser pulses from the laser source 114, e.g., a second laser pulse, and/or a laser beam, which may be a continuous wave laser beam or a pulsed laser beam. The pulsed laser beam can comprise a sequence of laser pulses, which may be identical to the first and/or second laser pulses. Preferably, the control unit 122 is configured to control an average power of the laser beam, e.g., through the pulse shaping unit 124, in particular such that the average power of the laser beam is much less than the average power of the first laser pulse. For example, the laser beam may comprise pulses with a pulse energy that is less than 10%, preferably less than 1% of the pulse energy of the first laser pulse.

The control unit 122 further comprises a focusing module 126, which is configured to control the position the focus 118. For this, the focusing module 126 may be configured to move the reservoir 106 and/or the objective 116, e.g., by controlling translation stages (not shown) that the reservoir 106 and/or the objective 116 are mounted on. In one example, the reservoir 106 may be placed on a two-axis translation stage that is capable of moving the reservoir 106 in a horizontal plane as illustrated by the horizontal arrow in FIG. 1 and the objective 116 may be mounted on a linear translation stage providing vertical travel as illustrated by the vertical arrow in FIG. 1. Alternatively, the reservoir 106 and/or the objective 116 may be movable in three orthogonal directions. In another example, the focusing module 126 may control the position the focus 118 by changing a propagation direction of the first laser pulse before passing through the objective 116. To this end, the focusing module 126 may for example control an adjustable mirror, e.g., with piezo actuators, a galvanometer scanner, an acousto-optic deflector, or an electro-optic deflector, which may enable a fast positioning of the focus 118. Alternatively or additionally, the focusing module 126 may be configured to change a spatial intensity pattern and/or a spatial phase pattern of the first laser pulse to position the focus 118, for example through a spatial light modulator like a digital micromirror device or a liquid crystal array. In this case, the focusing module 126 may be configured to simultaneously focus one or more laser pulses onto different foci. In another example, the focusing module 126 may be configured to adjust a focal length of a lens, e.g., the effective focal length of the objective 116 or the focal length of a focus-tunable lens placed in the optical path in front of the objective 116. The focusing module 126 may further be configured to control a motion of the substrate 104, e.g., for positioning it relative to the focus 118.

The control unit 122 comprises an imaging module 128, which is configured to determine a position of at least one of the cells 102 in the medium 108 at least in part, in particular a distribution of the cells 102. The imaging module 128 may be connected to a camera 130, e.g., a CCD camera or a CMOS camera, which is configured to image the cells 102 through an imaging system 132. The imaging system 132 may for example be a lens which in conjunction with the objective 116 images an image layer within the reservoir 106 onto an image sensor of the camera 130. The imaging system 132 may comprise additional optical elements. Furthermore, the imaging system 132 may be configured to image different planes within the reservoir without moving the objective 116 and may be configured to image a plane that does not contain the focus 118, for example a plane in the surface layer containing the cells 102 or a plane on or adjacent to the acceptor surface 112. To image the distribution of the cells 102, the device 100 may also comprise a light source 134 to illuminate the image plane. Light from the light source 134 may be directed at the image plane through the objective 116 or along an optical path that does not pass through the objective, e.g., from the opposing side of the reservoir 106 as compared to the objective 116. The light source 134 may be a broadband light source, e.g., a halogen lamp or a light-emitting diode, or may be a monochromatic light source like a laser. In particular, the light source 134 may emit light at a wavelength that is suitable for exciting optical labels attached to the cells 102, e.g., fluorophores, quantum dots or nitrogen-vacancy centers. The light emitted by the light source 134 may be overlapped with the optical path of the imaging system 132 using a mirror 136, in particular a dichroic mirror. Correspondingly, the mirror 120 may also be a dichroic mirror, e.g., a dichroic mirror configured to transmit one or more wavelengths associated with the imaging and to reflect the center wavelength of the laser source 114.

The camera 130, the imaging system 132, and the light source 134 may for example be configured to perform a contrast imaging method, e.g., linear contrast methods, non-linear contrast methods or super-resolution techniques such as photoactivated localization microscopy (PALM) or stochastic optical reconstruction microscopy (STORM). Linear contrast methods include e.g., single-photon absorption imaging, single-photon transmission imaging and single-photon fluorescence imaging. Nonlinear contrast methods include e.g., two-photon fluorescence imaging, second or third harmonic generation and coherent anti-Stokes Raman spectroscopy (CARS).

The imaging module 128 may be configured to obtain an image of the distribution of the cells 102 from the camera 130 and may be configured to analyze this image, e.g., to identify one or more single cells and to determine their positions. To this end, the imaging module 128 may be configured to execute pattern recognition algorithms and/or fitting procedures. The imaging module 128 may be configured to distinguish different types of biological cells and to determine their distribution individually, for example by determining the size and/or shape of cells 102 in an image or by detecting cell-type specific markers, e.g., fluorescent labels. The imaging module 128 may further be configured to provide the image to an external device, for example a computer, a display and/or a data storage device (not shown). The imaging module 128 may further be configured to receive a region of interest, e.g., from a user via an input, in which a single cell is to be identified. The imaging module 128 can also be configured to obtain an image of the acceptor surface 112, for example to determine a distribution of cells transferred to the acceptor surface 112 or to identify or select a target position on the acceptor surface 112. Furthermore, the imaging module 128 can be configured to determine a position of the reservoir 106, the substrate 104 and/or the focus 118 and to provide this position to the focusing module 126.

In addition to the components shown in FIG. 1, the device 100 can have additional components. The reservoir 106 and the substrate 104 can for example be contained in a transfer chamber 160, which is shown e.g., in FIG. 2b-2f. The transfer chamber 160 can in particular be an incubation chamber, which may be temperature-controlled. For this, the device 100 may comprise one or more temperature sensors, a heating element, a cooling element and/or a temperature control unit (not shown). The device 100 may further be combined with an optical microscope, for example a confocal microscope or a fluorescence microscope (not shown).

Figure 2A:
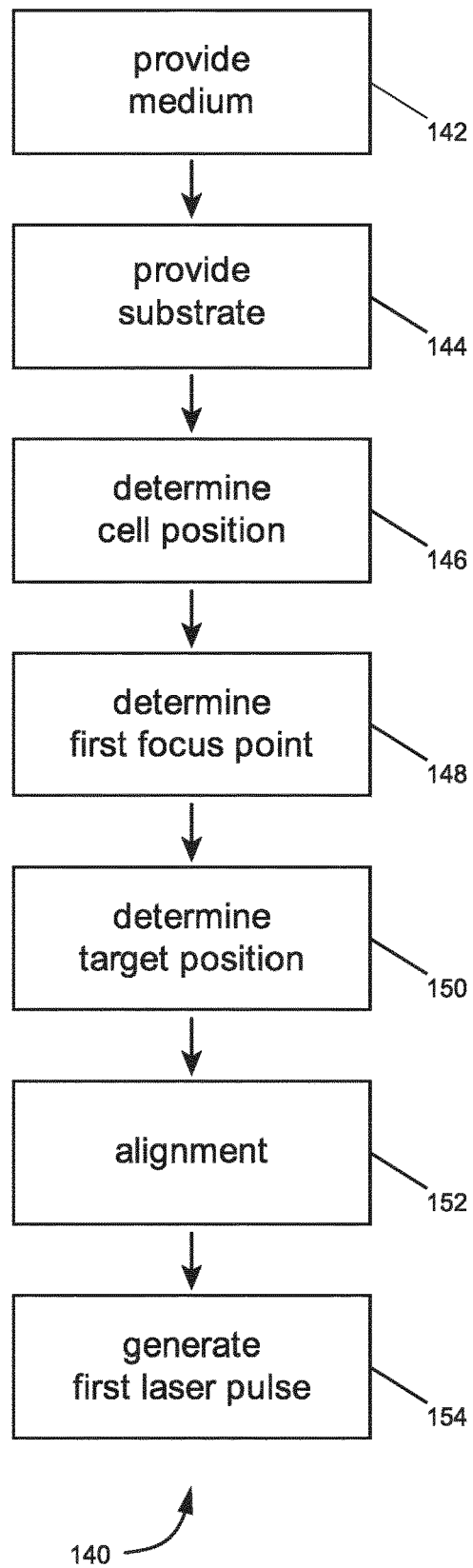
FIG. 2a: a flow chart of a method to transfer objects onto a substrate in accordance with an embodiment of the invention.
Figure 2F:
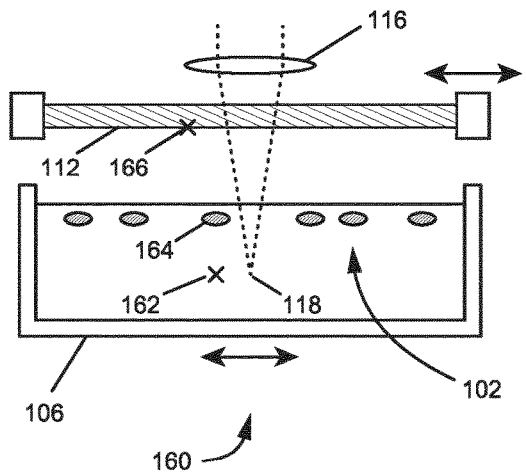
Figure 2F:
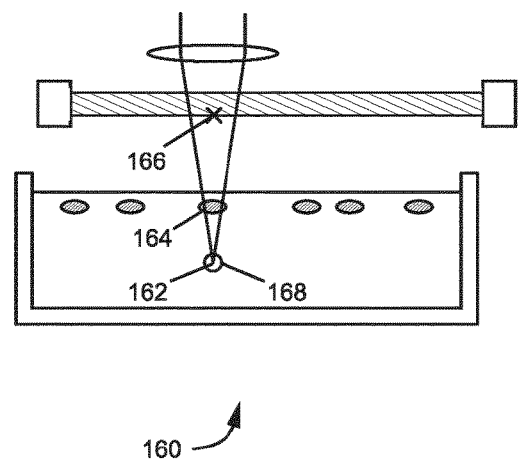
Figure 2F:
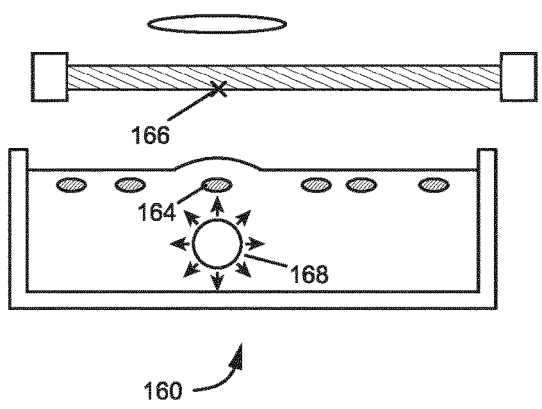
Figure 2F:
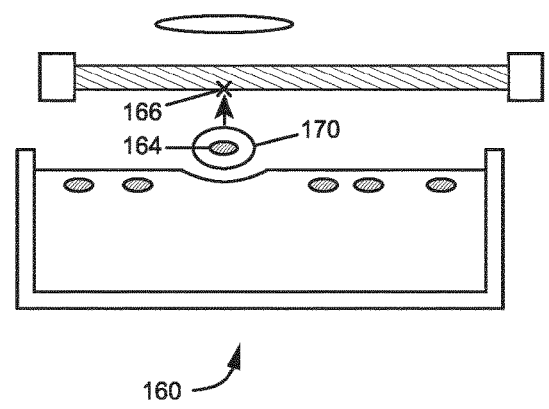
Figure 2F:
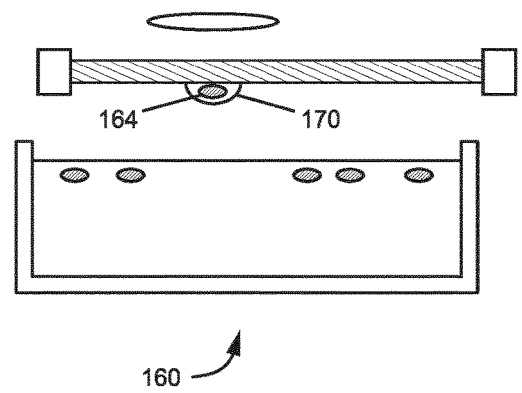

FIG. 2a shows a flow chart of a method 140 for transferring objects, in particular biological objects like biological cells, onto a substrate according to an embodiment of the invention. FIGS. 2b-2f schematically illustrate some of the steps of the method 140. In the following, the method 140 is described with reference to the device 100 and its components as depicted in FIG. 1, wherein the objects 102 are biological cells, but the method 140 may also be implemented using other devices and/or other objects according to various embodiments of the invention.

In step 142, the medium 108 is provided in the reservoir 106, wherein the medium 108 contains the cells 102. The cells 102 may be added to the medium 108 prior to or after filling the medium 108 in the reservoir 106. The step 142 may include an incubation period, during which the medium 108 is incubated in the reservoir 106, for example when a density gradient medium is used in order to let the cells 102 accumulate in the surface layer of the medium 108 or to achieve a homogeneous distribution of the cells 102 throughout the medium 108 or in the surface layer. In some examples, providing the medium 108 may comprise creating a flow of the medium 108 in the reservoir 106, e.g., using a lab-on-a-chip system as the reservoir 106, e.g., for cell sorting.

The substrate 104 is provided in step 144 by mounting or placing it in the substrate holder 110 such that the acceptor surface 112 faces an opening of the reservoir 106. This step may comprise coating the acceptor surface 112 with a medium, which may be identical to the medium 108. In another example, the acceptor surface 112 may already have been coated beforehand. In particular, the acceptor surface 112 may be coated with a cushioning film to dampen the impact for cells that are transferred to the acceptor surface 112. The cushioning film may further provide a suitable environment for the transferred cells and may contain extracellular matrix proteins, e.g., to protect the cells from drying out and/or to enhance cell adhesion to the substrate. In some examples, the substrate 104 may be a lab-on-a-chip system, e.g., a lab-on-a-chip system configured to create a flow of an acceptor medium that cells are to be transferred to, e.g., for cell sorting.

Subsequently, a position of at least one of the cells 102 in the medium 108, preferably a distribution of the cells 102 in the medium 108, is determined at least in part in step 146. This can for example be done by taking one or more images of the cells 102 with the camera 130, which may be analyzed automatically by the imaging module 128 or manually by a user, e.g., to determine the position of one or more of the cells 102 or to determine a spatial density of the cells 102 in at least a part of the medium 108.

In step 148, a first target focus point 162 is determined relative to the position of the at least one cell as illustrated in FIG. 2b. The first target focus point 162 can for example be determined by identifying a single cell 164 and determining the position of the single cell 164 at least in part, e.g., by determining the position of the single cell 164 in the horizontal plane, i.e., the plane parallel to the surface of the medium 108. The first target focus point 162 may be chosen using the position of the single cell 164 as a reference. In particular, the first target focus point 162 may be aligned with the position of the single cell 164 in the horizontal plane, e.g., by placing the first target focus point 162 behind the single cell 164 along the vertical direction as seen from the acceptor surface 112. The position of the first target focus point 162 along the vertical direction may be kept at a fixed position relative to the position of the reservoir 106. Preferably, the vertical position of the first target focus point 162 is set at a predefined distance from the surface of the medium 108, i.e., the surface of the medium 108 facing the opening of the reservoir 106 and thus the acceptor surface 112, to facilitate the generation of a droplet of medium 108 by the first laser pulse. This predefined distance may be larger than an average distance of the cells 102 from the surface of the medium 108 in order to ensure that first target focus point 162 is located behind the cells 102 and in particular the cell 164 as seen from the acceptor surface 112. The predefined distance may be less than 300 µm, preferably less than 100 µm. The step 148 may comprise determining a position of the surface of the medium 108 to position the first target focus point 162 appropriately in the vertical direction.

The method 140 can further comprise determining a target position 166 on the acceptor surface 112 in step 150. The target position 166 may for example be specified by a user, e.g., by providing the respective coordinates or certain boundary conditions, or may be determined by identifying one or more features on the acceptor surface 112. This may e.g., be a dent, a bump, a groove and/or another cell on the acceptor surface 112, relative to which the target position 166 may be chosen. Alternatively, the target position 166 may not be specified, but simply be chosen as the position on the acceptor surface 112 opposing the cell 164.

Subsequently, the focus 118 can be aligned to the first target focus point 162 in step 152 such that the focus 118 is located at the position of the first target focus point 162. As described above, this can for example be done by moving the reservoir 106 and/or the objective 116 using translation stages as indicated by the arrow underneath the reservoir 106 in FIG. 2b. Alternatively or additionally, the focus 118 may be moved by adjusting a propagation direction of first laser pulse before passing through the objective 116, by adjusting a spatial intensity pattern and/or a spatial phase pattern of the first laser pulse and/or by changing a focal length of a lens. To facilitate the alignment, the control unit 122 may be configured to generate an alignment beam, e.g., from the laser source 114 or the light source 134, in order to indicate the current position of the focus 118, which may for example be imaged with a camera, e.g., camera 130, and may be used as active feedback for the alignment process. During the alignment procedure, a distribution of the cells 102, in particular the position of the cell 164, may be monitored and the first target focus point 162 may be updated accordingly, e.g., to adjust for a motion of the cells 102 while aligning the focus 118. In one example, the focus 118 may be aligned in the horizontal plane by changing the propagation direction of the first laser pulse, e.g., with the adjustable mirror 120, a galvanometer scanner, an acousto-optic modulator or an electro-optic modulator, and in the vertical direction by changing the divergence of the first laser pulse, e.g., by moving a lens or by changing a focal length of a lens.

Step 152 may further comprise aligning the target position 166 on the acceptor surface 112 with the first target focus point 162 in the horizontal plane, e.g., moving the substrate 104 such that the target position 166 is located above the first target focus point 162 in the vertical direction. After the alignment step 152, the acceptor surface 112 and the reservoir 106 may for example be positioned as shown in FIG. 2c, i.e., both may be displaced horizontally with respect to the optical axis of the objective 116.

In step 154, the first laser pulse is then generated from the laser source 114 by the control unit 122 and focused through the objective 116 onto the focus 118, which is overlapped with the first target focus point 162. Due to the high intensity of the first laser pulse at the first target focus point 162, a cavitation bubble 168 can form in the vicinity of the first target focus point 162. The cavitation bubble 168 may for example be created by photoionization processes, which may lead to an optical breakdown of the medium 108, in particular non-linear photoionization processes, in which multiple photons from the first laser pulse ionize a molecule or an atom in the medium 108. The photoionization may lead to the formation of a high pressure plasma and a rapid increase in temperature in the vicinity of the first target focus point 162, which may drive a phase transition into a gas phase and thereby create the cavitation bubble. In another example, non-linear absorption of multiple photons by molecules or atoms in the medium can lead to a rapid increase in temperature in the vicinity of the first target focus point 162, which may drive a phase transition into a gas phase and thereby create the cavitation bubble.

The cavitation bubble 168 may subsequently expand rapidly as illustrated in FIG. 2d. When the cavitation bubble 168 approaches a surface of the medium 108, a droplet 170 of the medium 108 may be ejected from the surface as shown in FIG. 2e. The droplet 170 may be a single droplet as in FIG. 2e, but may also be a jet of the medium 108 and/or consist of multiple droplets or multiple jets. If the first target focus point 162 is located underneath one or more cells, a cell may be ejected from the medium 108 together with the droplet 170, e.g., the cell 164. The droplet 170 may be ejected towards the acceptor surface 112 and, provided that the distance between the medium 108 and the acceptor surface 112 is chosen appropriately, may hit the acceptor surface 112. The distance between the medium 108 and the acceptor surface 112 required for this may for example be less than 3 mm. When the droplet 170 hits the acceptor surface 112, the cell 164 may stick to the acceptor surface 112. To increase the probability of an ejected cell 164 to remain on the acceptor surface 112, the acceptor surface 112 may be patterned or structured and/or coated by a suitable medium, preferably one containing extracellular matrix proteins as described above.

To allow for a controlled transfer of a single cell, the cell 164 may be picked from the plurality of cells 102 such that the distance to neighboring cells is as large as possible or at least sufficiently large to avoid transfer of other cells. In addition, the first target focus point 162 may be determined based on the distribution of the cells 102 such that the probability to transfer other cells is minimized. For example, if there are two other cells in the vicinity on opposite sides of the cell 164, the first target focus point 162 may be chosen such that it lies in the center between two other cells in the horizontal plane as opposed to placing it directly underneath the position of the cell 164. After the first laser pulse has been focused onto the first target focus point 162, the method 140 may further comprise taking an image of the acceptor surface 112 to confirm that the cell 164 has been transferred successfully and/or to determine the position of the cell 164 on the acceptor surface 112.

Figure 3A:
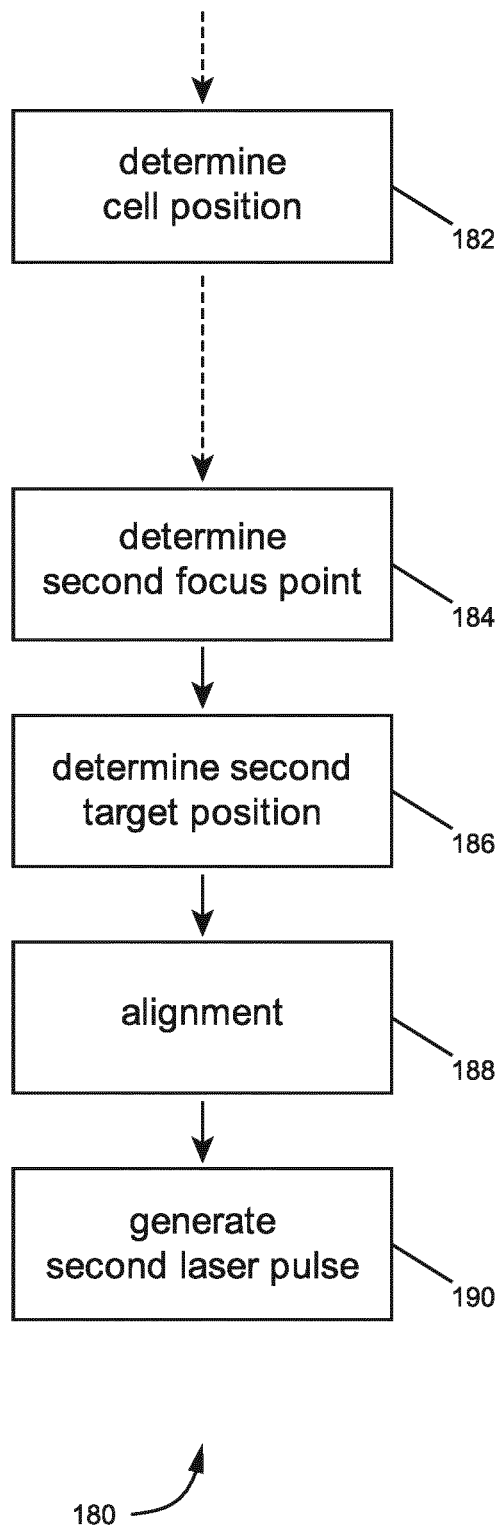
FIG. 3a: a flow chart of a method to transfer objects onto a substrate using two laser pulses in accordance with an embodiment of the invention.
Figure 3B:
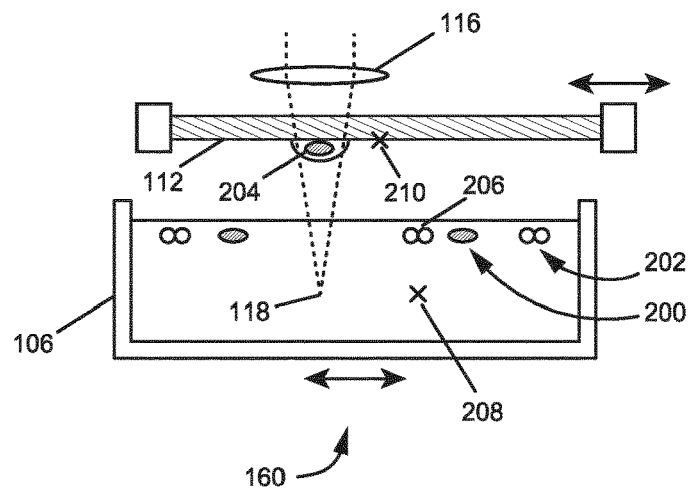
FIG. 3b-3d: a cell-type specific laser-induced transfer of single cells according to an embodiment of the invention.
Figure 3C:
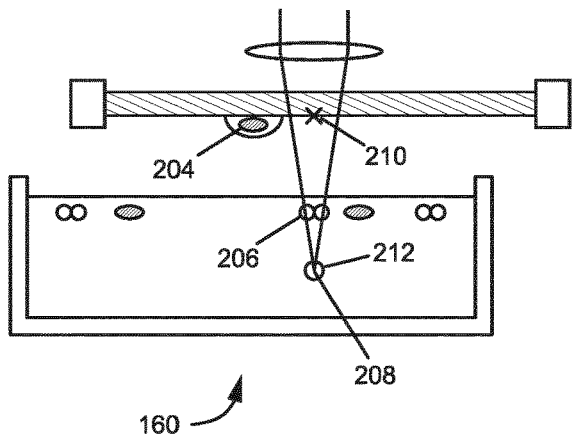
Figure 3D:
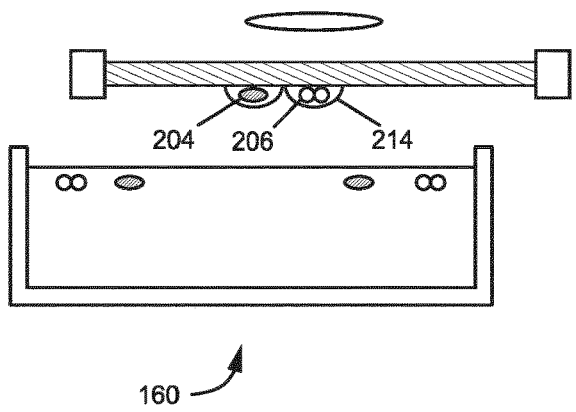

FIG. 3a depicts a flow chart of a method 180 for transferring objects, in particular biological objects like biological cells, onto a substrate using two laser pulses according to an embodiment of the invention. An exemplary implementation of this method 180 with the device 100 to transfer two single cells of different types to the acceptor surface 112 is illustrated in FIGS. 3b-3d, but the method 180 may also be implemented using other devices and/or other objects according to various embodiments of the invention.

The method 180 begins by providing the medium 108 and the substrate 104 similar to steps 142 and 144 in FIG. 2a, which is omitted in the flow chart of FIG. 3a for clarity. The medium 108 may contain different types of cells, for example cells of a first type 200 and cells of a second type 202 as shown in FIG. 3b. The cells 200, 202 may be labeled by cell-type specific markers, e.g., fluorescent labels with different characteristic wavelengths.

In step 182, the position of at least one of the cells in the medium is determined similar as described above with respect to step 146. In addition, step 182 may comprise determining a type of the at least one cell of which the position in the medium is determined, e.g., through the cell-type specific markers. Alternatively, the cells 200, 202 may not be labeled, but may be distinguishable by other features, e.g., their size and/or shape. In one example, a cell 204 of the first type and a cell 206 of the second type are identified and their positions determined. In addition, the positions and types of other cells may be determined and the cells 204 and 206 may be single cells that are spatially isolated from other cells.

Subsequently, a first target focus point 162 is selected in the medium and a first laser pulse is generated and focused onto the first target focus point 162, e.g., similar to steps 148-154 of method 140. For example, the cell 204 of the first type may be transferred to a first target position 166 on the acceptor surface 112 as described above.

In addition, a second target focus point 208 can be determined in step 184, e.g., relative to the position of the cell 206 of the second type in order to transfer the cell 206 to the acceptor surface as well. The second target focus point 208 may be determined simultaneously with the first target focus point 162. The second target focus point 208 may be chosen similar to the first target focus point 162 as in step 148. Additionally, the first target focus point 162, the first target position 166 and/or the position of other cells on the acceptor surface 112 may be taken into account when determining the second target focus point 208. For example, the cell 206 may be chosen from the cells of the second type 202 because it is the cell that is closest to the position of cell 204 on the acceptor surface 112, e.g., to simplify an alignment procedure. In another example, the cell 206 may be chosen because it is far away from the first target focus point 162 and thus unlikely to be moved and/or damaged by the first laser pulse. If the first laser pulse is generated prior to executing step 184, step 184 may additionally include repeating step 182 to determine an updated position of the at least one cell.

Furthermore, a second target position 210 can be selected on the acceptor surface 112 in step 186. The second target position 210 may be determined similar to the determination of the first target position 166 as in step 150. The determination of the second target position 210 may take into account the first target position 166 and/or the position of other cells on the acceptor surface 112. For example, a target distance between cells 204 and 206 on the acceptor surface 112 may be specified and the target position 210 is chosen at a corresponding distance from the position of cell 204 after the transfer to the acceptor surface 112. Alternatively, the first target position 166 and the second target position 210 may be determined simultaneously.

In step 188, the focus 118 can be aligned to the second target focus point 208 similar to the procedure of step 152 described above. The second laser pulse is generated in step 190 and focused onto the second target focus point 208, wherein the second laser pulse may have the same pulse energy and/or pulse duration as the first laser pulse. Correspondingly, the second laser pulse may generate a cavitation bubble 212 similar to the cavitation bubble 168 generated by the first laser pulse. The cavitation bubble 212 can expand subsequently and create a droplet 214 that is ejected from the medium 108 towards the acceptor surface 112 and may comprise one or more cells. For example, if the second target focus point 208 is chosen to lie underneath the cell 206, the droplet 214 may transfer cell 206 to the acceptor surface.

The first laser pulse and the second laser pulse may be generated simultaneously or in close succession. For example, a laser pulse emitted by the laser source 114 may be split to generate the first and second laser pulses, e.g., using a beam splitter or a spatial light modulator. Alternatively, two separate pulses emitted by the laser source 114 can be used to generate the first and second laser pulses. The methods 140 and/or 180 may be extended to perform a plurality of transfer processes, e.g., by repeating steps 146 to 154 and/or steps 184 to 190 at least in part. In particular, the plurality of transfers may be performed in close succession, e.g., for high-throughput 3d bioprinting or sorting of cells. Transfer processes may for example be performed with a repetition rate in the range of 1 kHz to 1 MHz. This may e.g., be used to create 3d patterns of cells on the acceptor surface 112 or for rapid cell sorting, e.g., by using lab-on-a-chip systems as the reservoir 106 and/or the substrate 104.

Figure 4A:
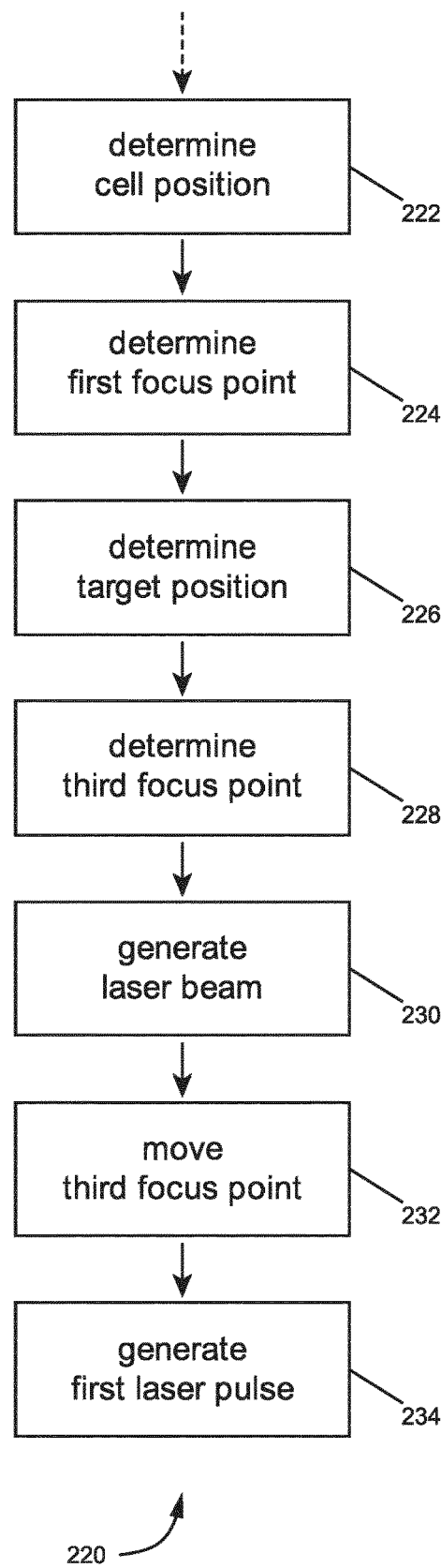
FIG. 4a: a flow chart of a method for transferring objects onto a substrate using an optical tweezer according to an embodiment of the invention.

In FIG. 4a, a flowchart of a method 220 is shown, which additionally employs an optical tweezer in accordance with an embodiment of the invention. The method 220 may for example be implemented with a device like device 100 and may be used to move a cell 164 with the optical tweezer prior to applying the first laser pulse as illustrated in FIGS. 4b-4e.

Similar to methods 140 and 180, the method 220 comprises providing the medium 108 and the substrate 104, which is not shown in the flowchart of FIG. 4a. Afterwards, the position of at least one of the cells 102 in the medium 108 is determined in step 222 similar to the procedures described above. In particular, the positions of a plurality of cells may be determined to obtain at least in part a distribution of the cells 102 in the medium 108.

In steps 224 and 226, a first target focus point 162 and a target position 166 are determined. The target position 166 may be obtained in a way similar to step 150 described above. The first target focus point 162 can be selected based on the distribution of cells 102 determined in step 222. For example, the first target focus point 162 may be chosen such that it is located in a region with a small number of cells and/or such that a distance to cells in the vicinity of the first target focus point 162 is maximized, e.g., in order to reduce the probability to accidentally transfer non-selected cells. Unlike the examples shown in FIGS. 2b and 3b, the first target focus point 162 may not be aligned with the position of a cell 164, which may be selected to be transferred to the acceptor surface 112. The cell 164 may e.g., be chosen to be the cell that is closest to the first target focus point 162 and/or the target position 166 or may be chosen because of its properties.

In step 228, a third target focus point 242 is determined onto which a laser beam is to be focused in step 230. The laser beam may be a laser pulse, a sequence of laser pulses or a continuous wave laser beam and may be generated from the laser source 114 or from a different laser source. In one example, the laser beam is a pulsed laser beam from the laser source 114, which continuously emits pulses with a fixed repetition rate, wherein each of the pulses has the same duration as the first laser pulse. The laser beam may for example be used as a cutting tool, e.g., to cut tissue and/or to isolate cells of interest. In another example, the laser beam can serve as an optical tweezer, which may e.g., be used to localize and/or move cells 102 in the medium 108. In this case, the pulses of the laser beam may have a much lower pulse energy than the first laser pulse, e.g., 1% of the pulse energy of the first laser pulse, in order to avoid damaging the cells or disturbing the medium. This may be achieved by an attenuation of the output of the laser source 114.

The optical tweezer may for example be used to localize the cell 164 relative to the first target focus point 162 by choosing the third target focus point 242 such that it overlaps with the first target focus point 162. When the laser beam is focused onto the third target focus point 242, it can create a confining potential for the cells 102 with a shape determined by the intensity distribution of the laser beam and a minimum at the position of the third target focus point 242. Thereby, the cell 164 may be trapped at a position, e.g., to ensure that the position of the cell 164 remains aligned with the first target focus point 162. Depending on the intensity of the laser beam, the cell 164 may only be trapped in the horizontal plane, for example if a dipole force created by the confining potential is not sufficient to overcome a buoyancy that the cell 164 experiences in the medium 108.

Figure 4B:
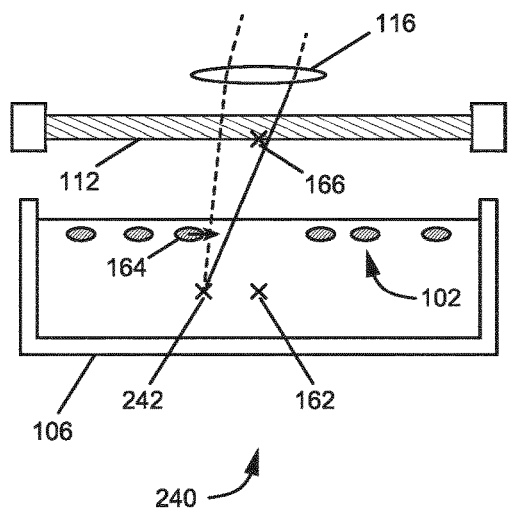
FIG. 4b-4e: trapping, moving, and transferring a single cell with an optical tweezer in accordance with an embodiment of the invention.
Figure 4C:
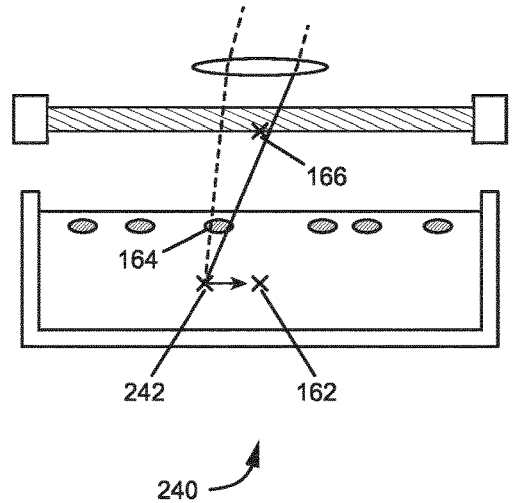
Figure 4D:
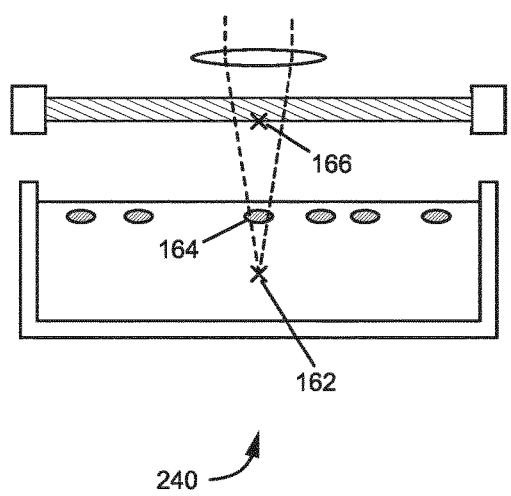
Figure 4E:
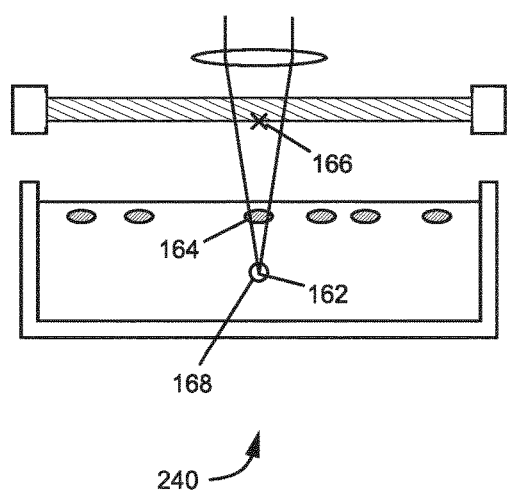

In another example, if the position of the cell 164 is not aligned with the first target focus point 162, the optical tweezer may be used to move the cell 164 to the first target focus point 162. The third target focus point 242 may be chosen to be aligned with the position of the cell 164 or to be in the vicinity of the position of cell 164. After switching on the laser beam, the cell 164 may be dragged towards the center of the laser beam in the horizontal plane as indicated by the arrow in FIG. 4b. Subsequently, the third target focus point 242 may be moved in step 232, while the laser beam is on and focused onto the third target focus point 242. If the cell 164 is trapped in the laser beam and the confining potential is sufficiently strong, the cell 164 may follow the motion of the third target focus point 242. The focus of the laser beam may be moved by the focusing module 126 as described above, e.g., by changing a propagation direction of the laser beam in front of the objective as illustrated in FIGS. 4b-4d. If the third target focus point 242 is moved to the first target focus point 162, the position of the cell 164 can thereby be aligned with the first target focus point 162 as shown in FIG. 4d. Once the cell 164 is aligned with the first target focus point 162, the first laser pulse may be generated and focused onto the first target focus point 162 in step 234, e.g., in order to transfer the cell 164 to the target position 166 on the acceptor surface 112.

The optical tweezer may further be used in other ways to alter the distribution of cells 102 in the medium 108 before applying the first laser pulse. For example, multiple cells may be moved to the same position such that multiple cells can be transferred to the acceptor surface 112 with the first laser pulse. In another example, a cell 164 is selected for transfer and the optical tweezer is employed for removing other cells from the vicinity of cell 164. The focusing module 126 may also be configured to align the focus of the laser beam to a third target focus point located on or close to the acceptor surface 112, for example to move cells on the acceptor surface 112 after transfer.

In some examples, the third target focus point 242 may be chosen adjacent to or on the acceptor surface 112, for example to perform subtractive or additive laser processing of the substrate 104, the acceptor surface 112 and/or a medium on the acceptor surface 112, e.g., by laser ablation or multi-photon polymerization. Thereby, structures like 3d patterns, scaffolds or extra-cellular matrix structures may be formed on the acceptor surface 112. The acceptor surface 112 may for example be coated by a medium to be structured, e.g., a medium containing riboflavin or a polymer gel with a temperature-dependent viscosity.

The flow charts shown in FIGS. 2a, 3a, and 4a only constitute specific examples for implementations of a method according to the present invention, which may be altered in many ways. In particular, the ordering of the steps is exemplary only and, as far as technically feasible, the steps can be permuted and the methods can be performed in an arbitrary order. For example, the substrate 104 may be provided before providing the medium 108 or a target position 166 on the acceptor surface 112 may be selected prior to determining the first target focus point 162 and/or determining the position of the at least one cell.

Figure 5A:
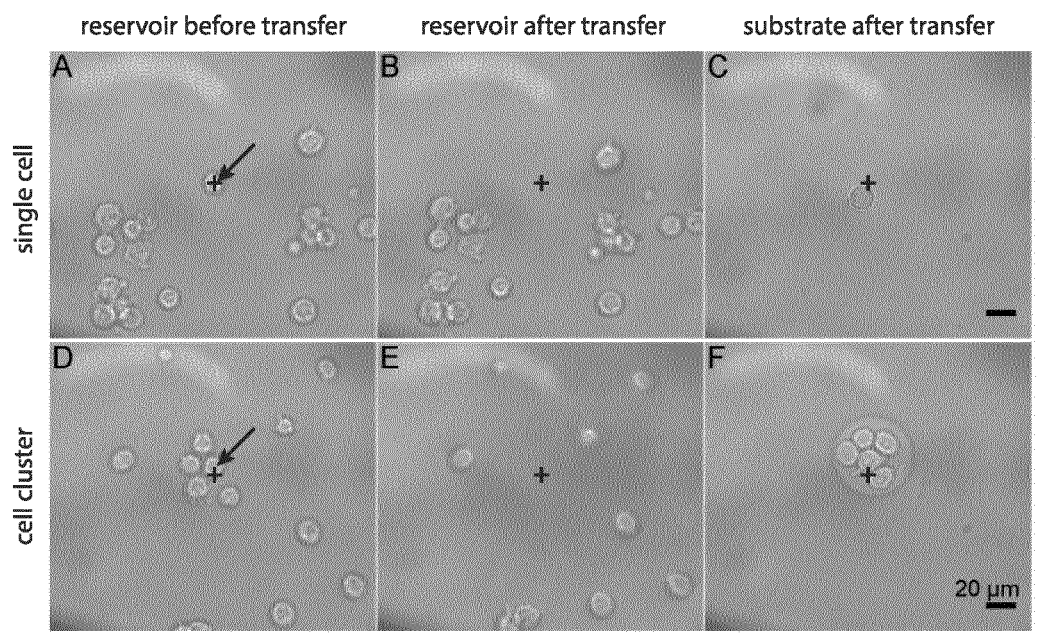
FIG. 5a-5c: experimentally obtained microscopic images of cell transfers using a device and methods according to exemplary embodiments of the invention.
Figure 5B:
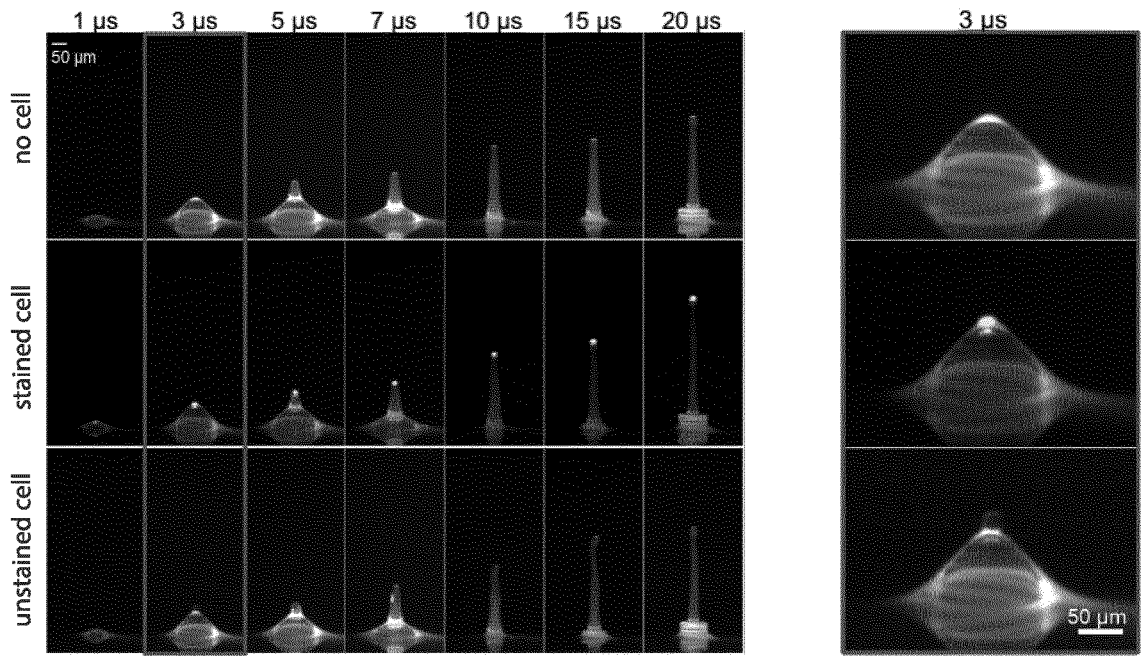
Figure 5C:
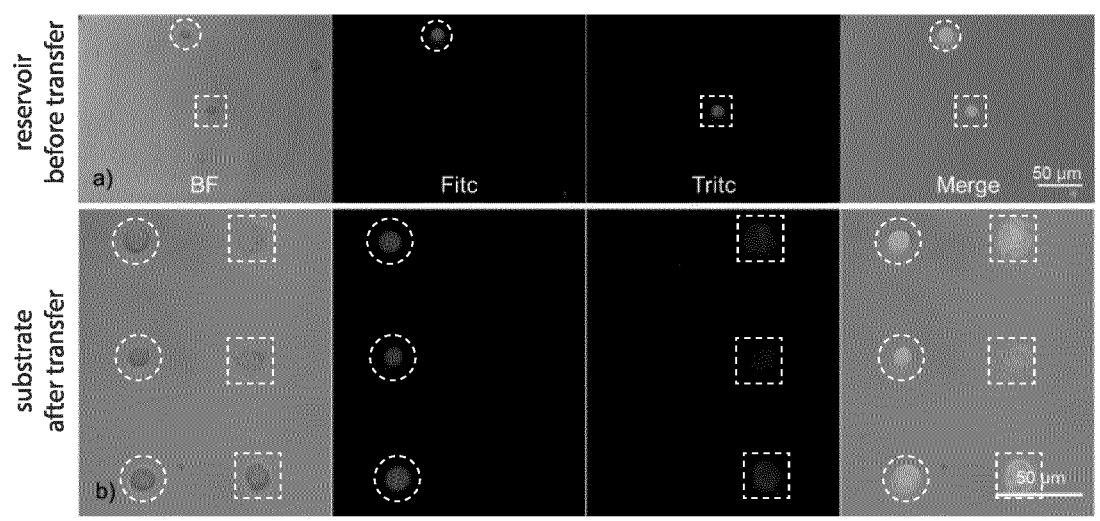

FIGS. 5a-5c depict experimentally obtained microscopic images of cell transfers using a device and method according to exemplary embodiments of the invention. In each experiment, a femtosecond laser pulse with a wavelength of 1030 nm, a pulse duration of 450 fs and a pulse energy of 2 µJ was generated and focused to a focus diameter of 1.6 µm, corresponding to a peak intensity of about $2 \cdot 10^{14}$ W/cm$^2$, at a depth of about 40 µm below the surface of a medium in a reservoir.

In FIG. 5a, the controlled transfer of a single cell (A-C) and of a cluster of multiple cells (D-F), respectively, is shown. The scale bar is 20 µm. The arrow indicates the cell and cell cluster, respectively, that is selected for transfer. The cell and the cell cluster are spatially separated from other cells in the reservoir. The cross indicates the horizontal position of the first target focus point, onto which the laser pulse is focused. The first target focus point is determined relative to the position of the cell and cell cluster, respectively. As can be seen in the images B, C and E, F, the laser pulses selectively transfer the cell and the cell cluster from the reservoir onto the substrate while the other cells remain in the reservoir.

FIG. 5b shows exemplary time traces of the droplet generation with and without cells. Each row contains a time-resolved series of fluorescence images taken at fixed times after firing the respective laser pulse. The plot on the right shows enlarged versions of the images taken 3 µs after firing the laser pulse. The scale bar is 50 µm. In each case, the laser pulse generates a jet that is ejected from the medium (Alexa Fluor 532 NHS-ester stained Histopaque). The upper row shows an example of a jet that only contains pure liquid and no cells. The center row shows an example of a jet containing a single, Alexa Fluor 532 NHS-ester stained B16F1 cell. The lower row shows an example of a jet containing a single, un-stained B16F1 cell.

FIG. 5c depicts images of the controlled sorting of different types of cells. White dashed circles mark SCP1 cells labeled with green fluorescent protein (GFP) and white dashed rectangles mark murine fibroblasts labeled with red fluorescent protein (RFP). The first column shows brightfield microscopy images, the second and third columns show fluorescence images taken at different wavelengths and the fourth column shows merged images of the two corresponding fluorescence images. The scale bar is 50 µm. As shown in the upper row, the SCP1 cells and the fibroblasts are initially provided in the same medium. Based on the fluorescent labels, the two types of cells may be distinguished and may be transferred to the substrate selectively by choosing the target focus point accordingly. By moving the substrate relative to the target focus point, the cells may be transferred to pre-determined target positions on the substrate. This allows for creating cell patterns on the substrate, e.g., arranging the cells in a regular array as shown in FIG. 5c.

The embodiments of the present invention disclosed herein only constitute specific examples for illustration purposes. The present invention can be implemented in various ways and with many modifications without altering the underlying basic properties. Therefore, the present invention is only defined by the claims as stated below.

LIST OF REFERENCE SIGNS

100—Device for transferring biological cells onto a substrate

102—Biological cells
104—Substrate
106—Reservoir
108—Medium
110—Substrate holder
112—Acceptor surface
114—Laser source
116—Objective
118—Focus
120—Mirror
122—Control unit
124—Pulse shaping unit
126—Focusing module
128—Imaging module
130—Camera
132—Imaging system
134—Light source
136—Mirror
140—Method for transferring biological cells onto a substrate
142—Step of providing the medium
144—Step of providing the substrate
146—Step of determining the position of at least one cell
148—Step of determining the first target focus point
150—Step of determining the target position
152—Step of aligning the focus and the target position
154—Step of generating the first laser pulse
160—Transfer chamber of a device for transferring biological cells onto a substrate
162—First target focus point
164—Single cell
166—Target position
168—Cavitation bubble
170—Ejected droplet
180—Method for transferring biological cells onto a substrate using two laser pulses
182—Step of determining the position of at least one cell
184—Step of determining the second target focus point
186—Step of determining the second target position
188—Step of aligning the focus and the second target position
190—Step of generating the second laser pulse
200—Cells of first type
202—Cells of second type
204—First single cell
206—Second single cell
208—Second target focus point
210—Second target position
212—Cavitation bubble
214—Ejected droplet
220—Method for transferring biological cells onto a substrate using an optical tweezer
222—Step of determining the position of at least one cell
224—Step of determining the first target focus point
226—Step of determining the target position
228—Step of determining the third target focus point
230—Step of generating laser beam
232—Step of moving the third target focus point
234—Step of generating the first laser pulse
240—Transfer chamber of another device for transferring biological cells onto a substrate
242—Third target focus point The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A method for transferring objects onto a substrate, the method comprising:
providing a medium in a reservoir, wherein the medium contains objects;
providing the substrate having an acceptor surface, wherein the acceptor surface faces an opening of the reservoir;
determining a first target focus point in the medium; and
generating a first laser pulse or first laser pulse train focused onto the first target focus point,
wherein:
one or both of a pulse intensity of the first laser pulse or first laser pulse train at the first target focus point and a pulse duration of the first laser pulse or first laser pulse train is/are chosen such that the first laser pulse or first laser pulse train generates a droplet of the medium that is ejected from the medium towards the acceptor surface;
a center wavelength of the first laser pulse or first laser pulse train is larger than 500 nm;
a position of at least one of the objects in the medium is determined at least in part by determining at least two spatial coordinates of the position of the at least one object; and
the first target focus point is determined relative to the position of the at least one object.

2. The method of claim 1, wherein the pulse intensity at the first target focus point exceeds a non-linear photoionization threshold of the medium.

3. The method of claim 1, wherein the objects are located in a surface layer in the vicinity of a surface of the medium facing the acceptor surface and the first target focus point is located on the opposite side of the surface layer as the acceptor surface.

4. The method of claim 1, wherein the first target focus point is located less than 300 μm below the surface of the medium facing the acceptor surface.

5. The method of claim 1, wherein the method further comprises:
imaging the objects in the medium to determine a distribution of the objects at least in part;
identifying a single object from the distribution of the objects, wherein the single object is spatially isolated from the other objects; and
determining the position of the single object at least in part;
wherein the first target focus point is determined relative to the position of the single object.

6. The method of claim 1, wherein the method further comprises aligning a focus of the first laser pulse or first laser pulse train to the first target focus point by at least one of the following:

changing a distance between an objective and the reservoir;

changing a propagation direction of the first laser pulse or first laser pulse train;

changing one or both of a spatial intensity pattern and a spatial phase pattern of the first laser pulse or first laser pulse train; and changing a focal length of a lens.

7. The method of claim 1, wherein the method further comprises determining a target position on the acceptor surface; and aligning the target position with the first target focus point along one direction.

8. The method of claim 1, wherein the acceptor surface is coated with a cushioning film.

9. The method of claim 1, wherein a diameter of the first laser pulse or first laser pulse train at the first target focus point is smaller than 5.0 μm.

10. The method of claim 1, wherein the first laser pulse is a femtosecond laser pulse or the first laser pulse train is a sequence of femtosecond laser pulses.

11. The method of claim 1, wherein one or both of the center wavelength and a spectral width of the first laser pulse or first laser pulse train is/are adapted to an absorption spectrum of the objects.

12. The method of claim 1, wherein the medium contains two or more types of objects and determining the position of the at least one object comprises determining the type of the at least one object.

13. The method of claim 1, wherein the method further comprises generating a plurality of laser pulses focused onto a plurality of target focus points in the medium to create a structure comprising a plurality of objects on the acceptor surface.

14. The method of claim 1, wherein the method further comprises focusing a laser beam onto a second target focus point in the medium and moving the second target focus point while the laser beam is focused onto the second target focus point.

15. A device for transferring objects onto a substrate, the device comprising:

a reservoir for holding a medium containing objects;

a substrate holder configured to hold the substrate having an acceptor surface such that the acceptor surface faces an opening of the reservoir;

a laser source configured to emit laser pulses;

a control unit for generating a first laser pulse or first laser pulse train from the laser source; and an objective for focusing the first laser pulse or first laser pulse train onto a focus of the first laser pulse or first laser pulse train;

wherein:

the control unit comprises an imaging module configured to determine a position of at least one of the objects in the medium at least in part by determining at least two spatial coordinates of the position of the at least one object;

the control unit is configured to determine a first target focus point relative to the position of the at least one object;

the control unit comprises a focusing module configured to align the focus of the first laser pulse or first laser pulse train to the first target focus point;

a center wavelength of the first laser pulse or first laser pulse train is larger than 500 nm; and a pulse intensity at the first target focus point and a pulse duration of the first laser pulse or first laser pulse train are sufficiently large such that the first laser pulse or first laser pulse train generates a droplet of the medium that is ejected from the medium towards the acceptor surface.

16. The device of claim 15, wherein the pulse intensity exceeds a non-linear photoionization threshold of the medium.

17. The device of claim 15, wherein the focusing module is configured to control the position the focus of the first laser pulse or first laser pulse train by at least one of the following:

changing a distance between the objective and the reservoir;

changing a propagation direction of the first laser pulse or first laser pulse train;

changing one or both of a spatial intensity pattern and a spatial phase pattern of the first laser pulse or first laser pulse train; and changing a focal length of a lens.

18. The device of claim 15, further comprising an imaging system and a camera for imaging the objects in the medium, wherein the imaging module is configured to:

determine a distribution of the objects at least in part;

identify a single object from the distribution of the objects, wherein the single object is spatially isolated from the other objects; and determine the position of the single object at least in part.

19. The device of claim 15, wherein the control unit is configured to move the substrate to align a target position on the acceptor surface with the first target focus point.

20. The device of claim 15, wherein the control unit is configured to adjust one or more of the center wavelength, a spectral width, the pulse duration and a pulse energy of the first laser pulse or first laser pulse train.

* * * * *